(12) United States Patent
Meder et al.

(10) Patent No.: US 9,938,580 B2
(45) Date of Patent: Apr. 10, 2018

(54) EPIGENETIC SIGNATURES AS MARKER FOR CARDIOMYOPATHIES AND MYOCARDIAL INSUFFICIENCIES

(71) Applicant: RUPRECHT-KARLS-UNIVERSITÄT HEIDELBERG, Heidelberg (DE)

(72) Inventors: Benjamin Meder, Dossenheim (DE); Jan Haas, Walldorf (DE); Hugo A. Katus, Heidelberg (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 14/384,955

(22) PCT Filed: Mar. 14, 2013

(86) PCT No.: PCT/EP2013/055267
§ 371 (c)(1),
(2) Date: Sep. 12, 2014

(87) PCT Pub. No.: WO2013/135830
PCT Pub. Date: Sep. 19, 2013

(65) Prior Publication Data
US 2015/0065355 A1    Mar. 5, 2015

Related U.S. Application Data

(60) Provisional application No. 61/610,841, filed on Mar. 14, 2012.

(51) Int. Cl.
*C12Q 1/68* (2006.01)
*C12P 19/34* (2006.01)
*C07H 21/02* (2006.01)

(52) U.S. Cl.
CPC ..... *C12Q 1/6883* (2013.01); *C12Q 2600/106* (2013.01); *C12Q 2600/112* (2013.01); *C12Q 2600/118* (2013.01); *C12Q 2600/154* (2013.01)

(58) Field of Classification Search
CPC ............ C12Q 1/6883; C12Q 2600/112; C12Q 2600/118; C12Q 2600/154
See application file for complete search history.

(56) References Cited

FOREIGN PATENT DOCUMENTS

WO    WO 02/00932 A2    1/2002

OTHER PUBLICATIONS

Movassagh M. et al. Epigenomics (Feb. 2011) 3(1), 103-109.*
Costello J.F. et al. (1994) The Journal of Biological Chemistry, 269,17228-17237.*
Chen, G. et al. Molecular & Cellular Proteomics 1.4 (2002) pp. 304-313.*
Cheung V.G. et al. Nature Genetics (Mar. 2003) vol. 33, pp. 422-425.*
Baccarelli, Andrea et al., "Ischemic heart disease and stroke relation to blood DNA methylation," *Epidemiology*, 2010, 21(6):819-828.
Buria, Sandra et al., "DNA methylation and Yin Yang-1 repress adenosine $A_{2A}$ receptor levels in human brain," *Journal of Neurochemistry*, 2010, 115(1):283-295.
Haas, Jan et al., "Alterations in Cardiac DNA methylation in human dilated cardiomyopathy," *EMBO Molecular Medicine*, 2013, 5(3):413-429.
Movassagh, Mehregan etal., "Differential DNA Methylation Correlates with Differential Expression of Angiogenic Factors in Human Heart Failure," *PLoS One*, 2010, 5(1):e8564.
Post, Wendy S. et al. "Methylation of the estrogen receptor gene is associated with aging and atherosclerosis in the cardiovascular system," *Cardiovascular Research*, 1999, 43(4):985-991.
Umeda, Patrick K. et al., "Epigenetic alterations in diabetic cardiomyopathy," *Progress in Experimental Cardiology*, 2001, 33(6):1.

* cited by examiner

*Primary Examiner* — Stephen T Kapushoc
(74) *Attorney, Agent, or Firm* — Saliwanchik, Lloyd & Eisenschenk

(57) ABSTRACT

The present invention relates to the use of DNA methylation profiles of patient samples for the diagnosis, prognosis and/or therapy monitoring of a heart disease in a patient, wherein the DNA methylation profile of the patient sample is compared with the DNA methylation profile of a control sample, and wherein a difference in the DNA methylation profile of the patient sample compared to the control sample is indicative of a heart disease or of the risk for developing a heart disease or for a prediction of therapy effects or therapy outcome. The present invention further relates to methods for the diagnosis, prognosis and/or therapy monitoring of a heart disease in a patient, comprising determining the DNA methylation profile in a patient sample comprising genomic DNA from heart cells, heart tissue or peripheral blood; and comparing the DNA methylation profile in the patient sample with the DNA methylation profile from a normal subject not having a heart disease or having a normal heart function. The present invention furthermore relates to kits that are suitable for the methods and uses of the invention. The present invention furthermore relates to the use of ADORA2A, ERBB3, LY75, HOXB13, GF11, CLDN4, FDX1, ID4, NAT1, PPARGC1A, SULF2, TFF1, TKT, ATP2C, CCDC59, GSTM5m, SLC9A6 and TDG as marker for the diagnosis, prognosis and/or therapy monitoring of a heart disease in a patient.

12 Claims, 16 Drawing Sheets

Figure 1 A and B
A
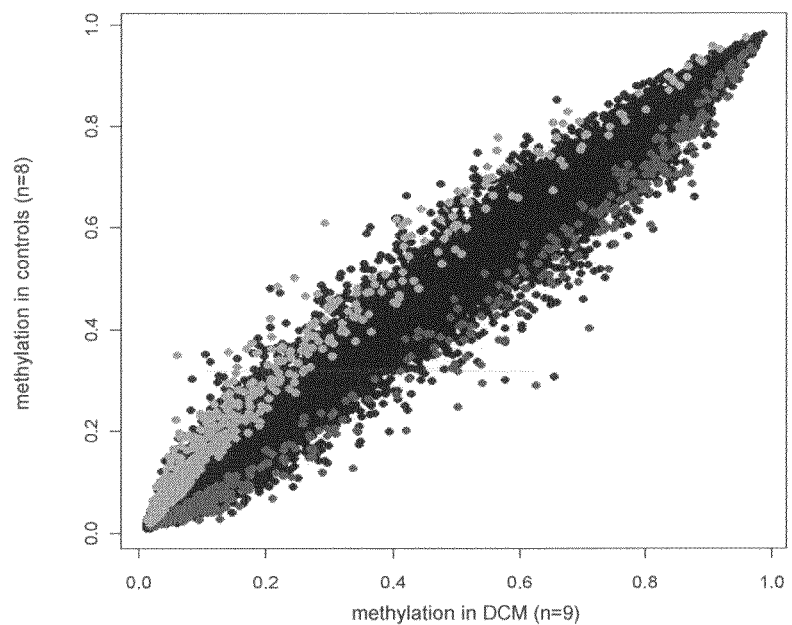
B
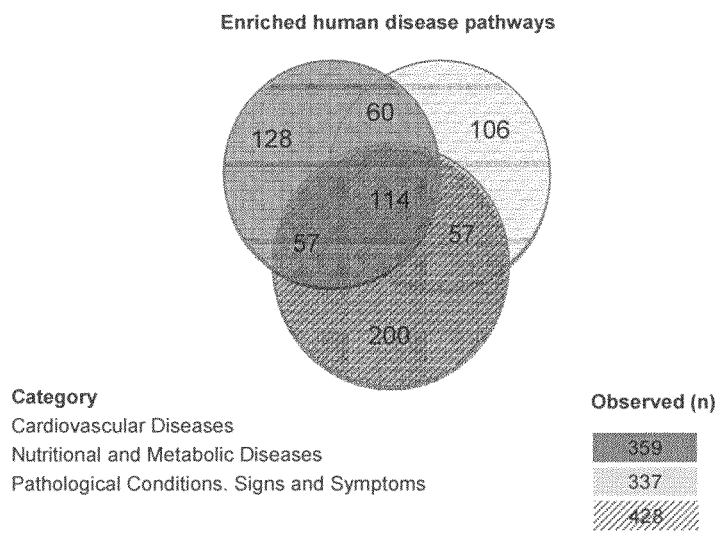

Figure 3 A and B
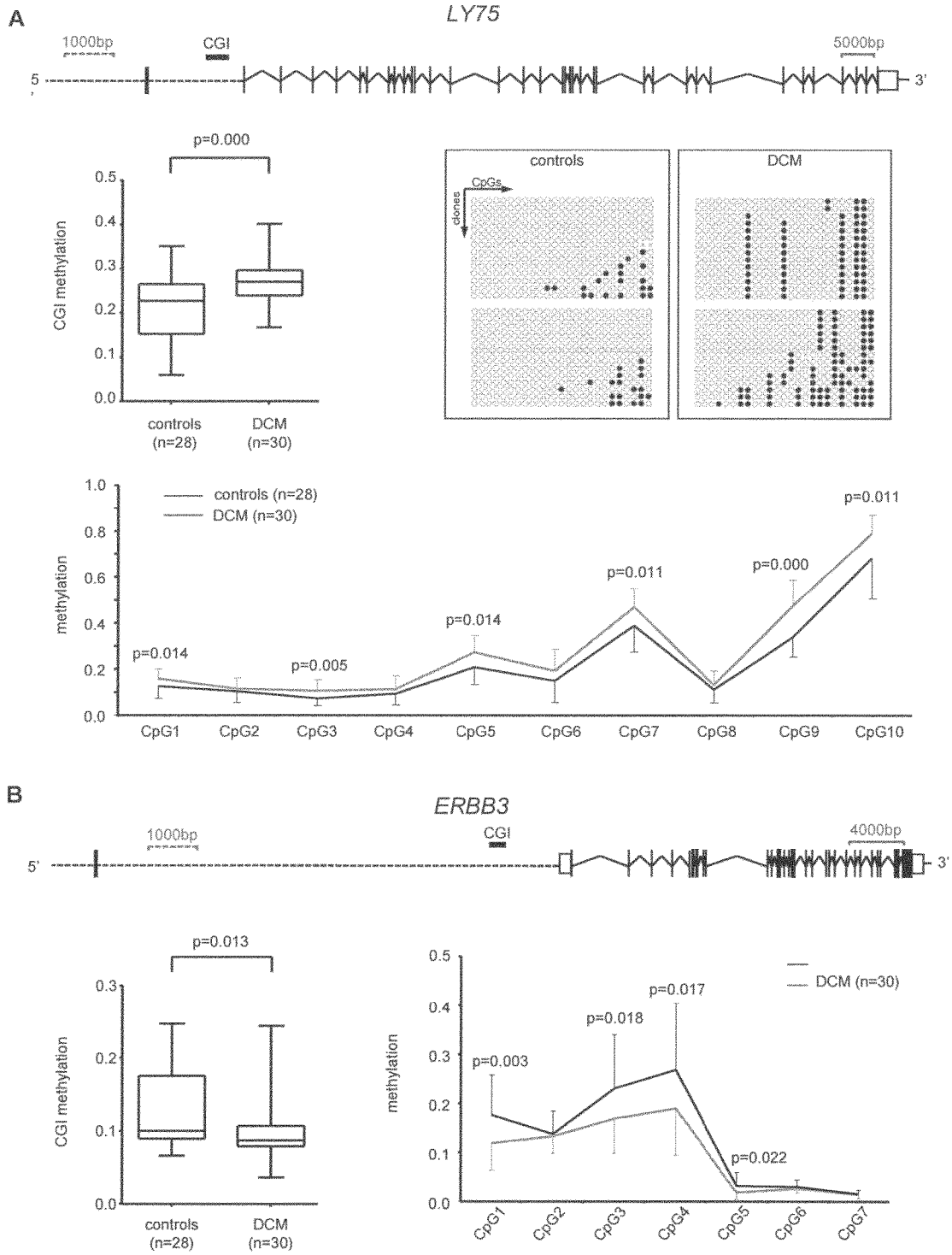

Figure 3 C and D
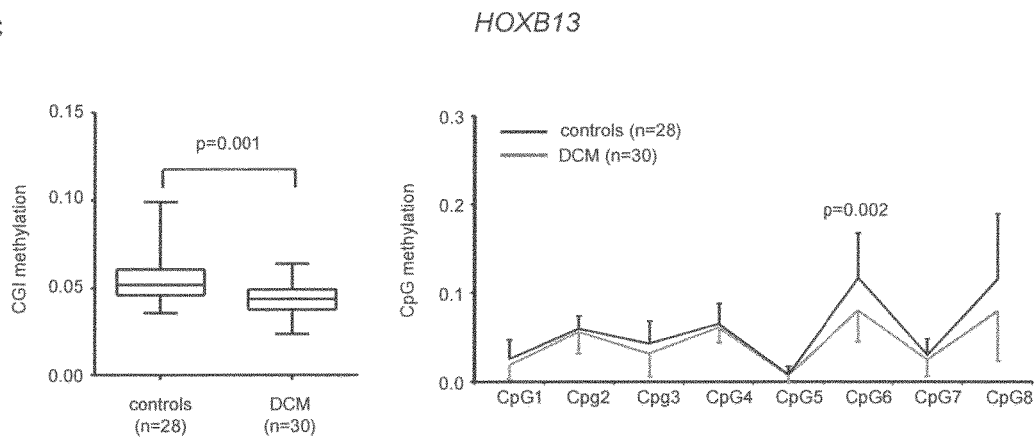
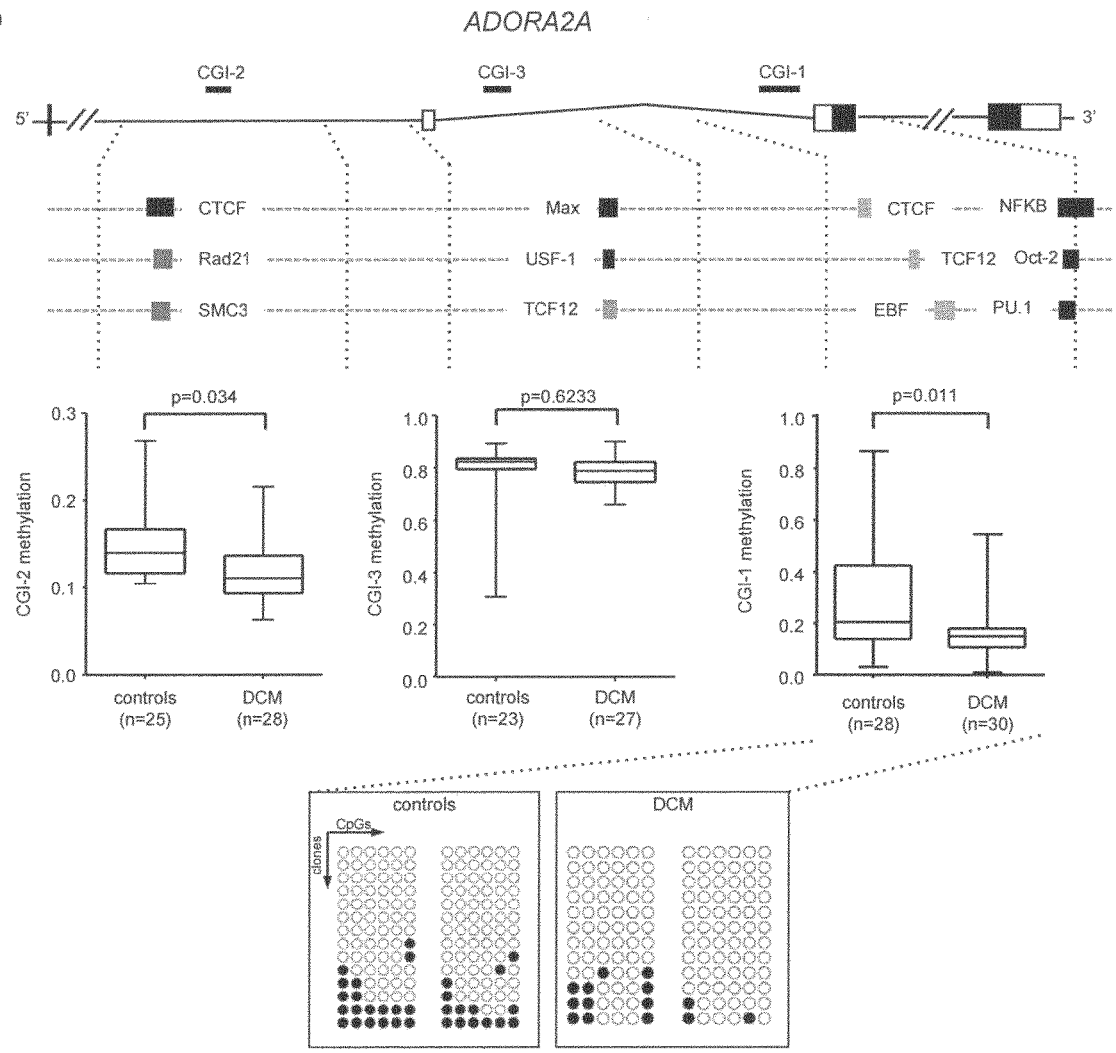

Figure 4 A-F
A
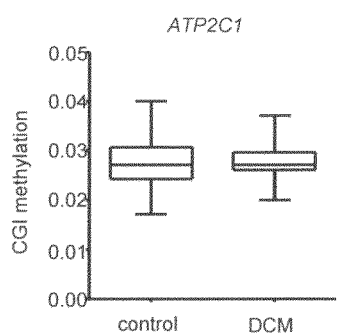
B
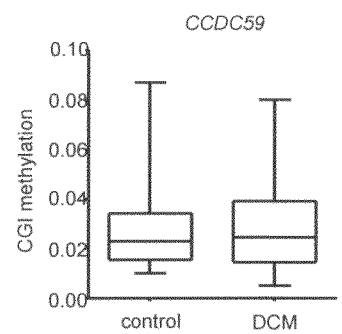
C
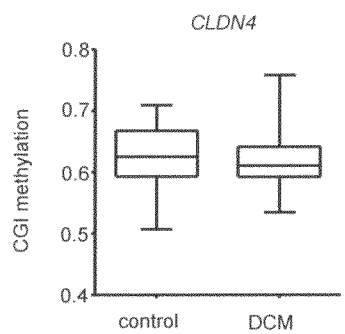
D
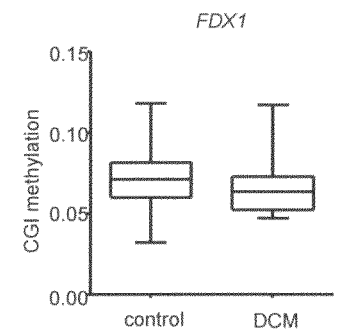
E
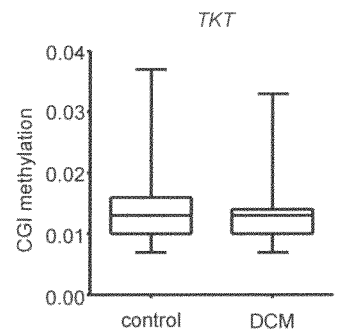
F
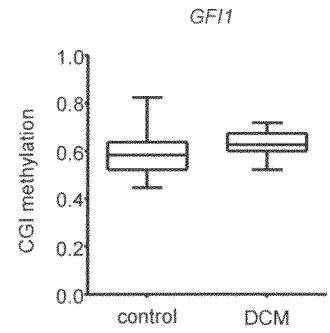

Figure 4 G-L
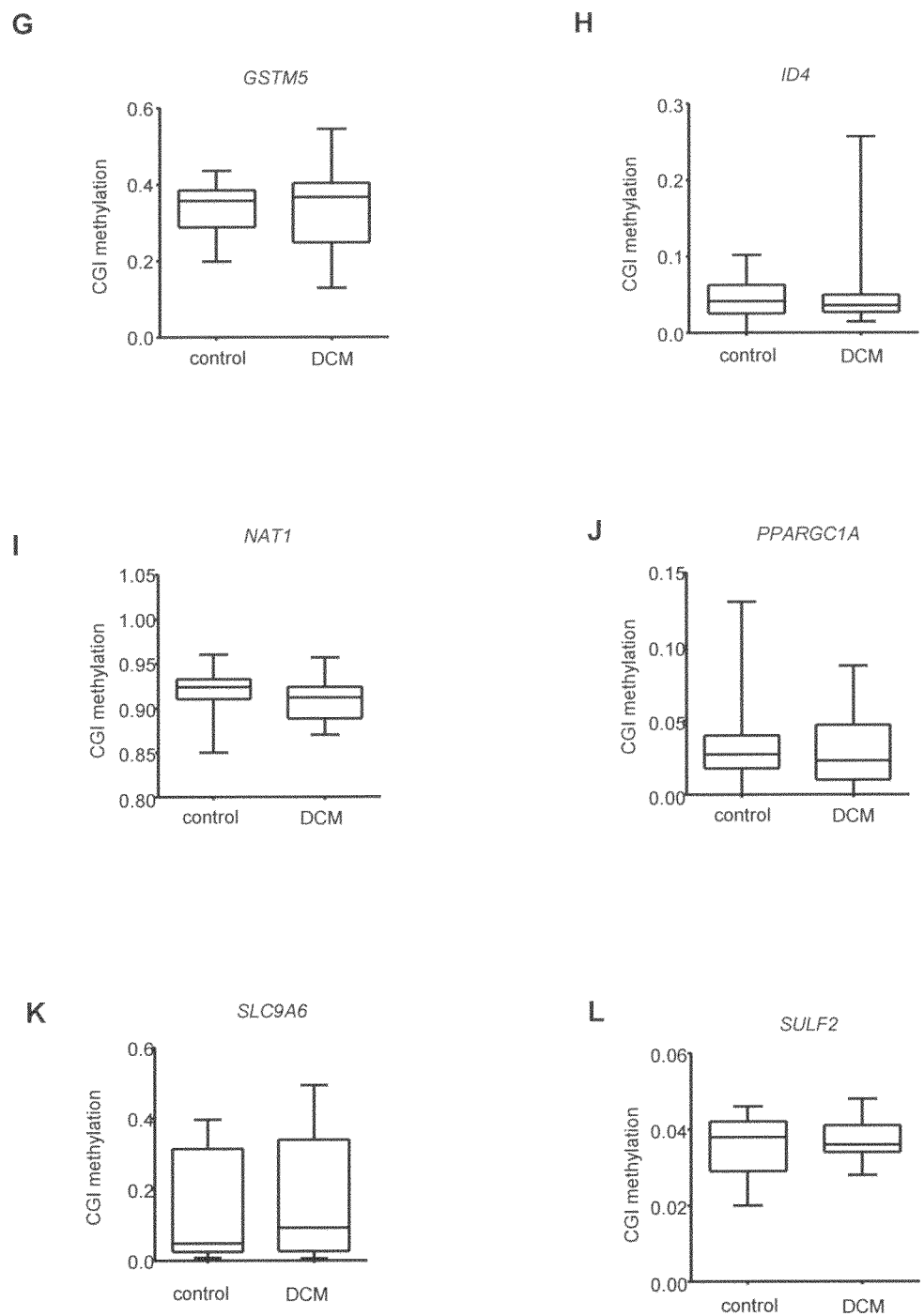

Figure 4 M-P
M
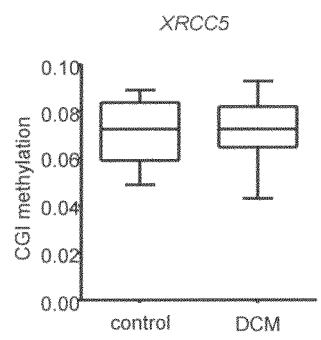
N
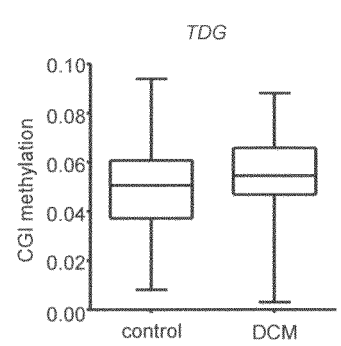
O
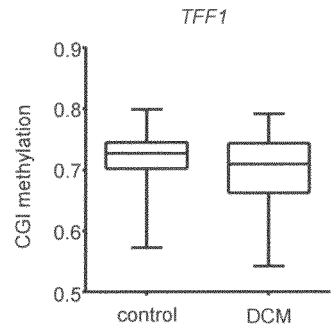
P
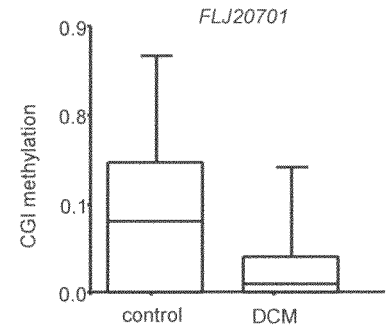

Figure 6
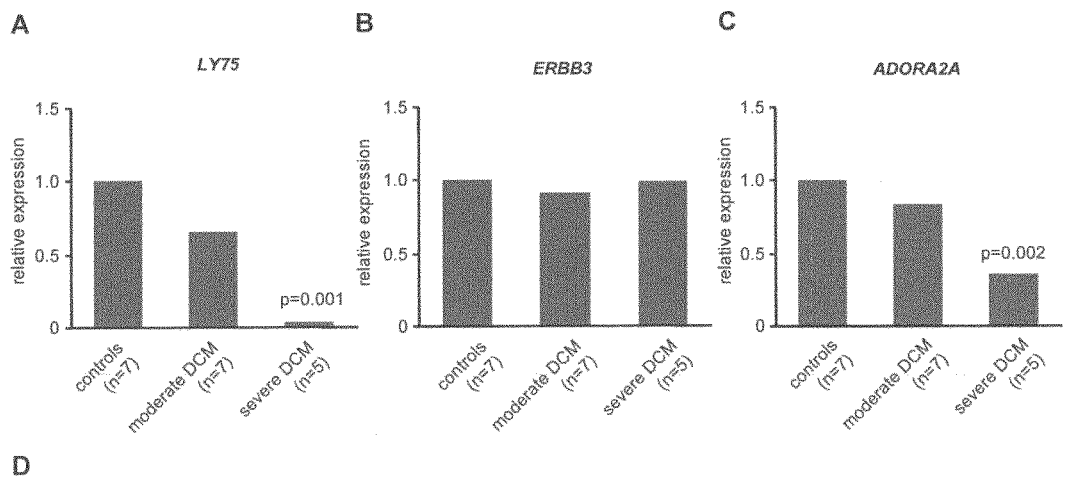
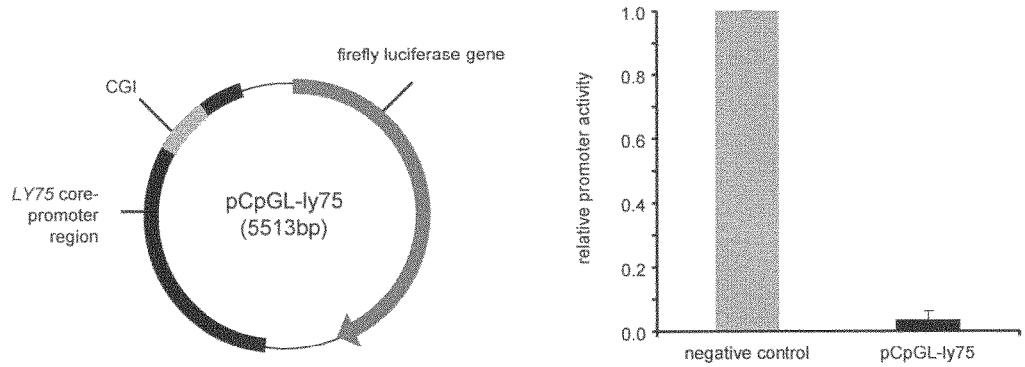
| | LY75 [ΔCT] | ERBB3 [ΔCT] | ADORA2A [ΔCT] |
|---|---|---|---|
| Controls (n=7) | 8.51 ± 0.66 | 9.88 ± 0.80 | 8.65 ± 0.26 |
| Moderate DCM (n=7) | 9.11 ± 0.40 | 10.02 ± 0.63 | 8.90 ± 0.53 |
| Severe DCM (n=5) | 13.11 ± 0.78 | 9.90 ± 0.53 | 10.08 ± 0.20 |

Figure 7
A
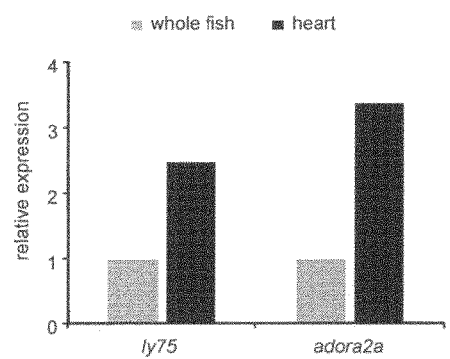
B
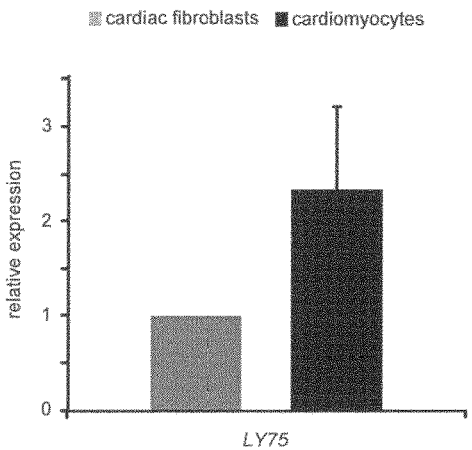
C
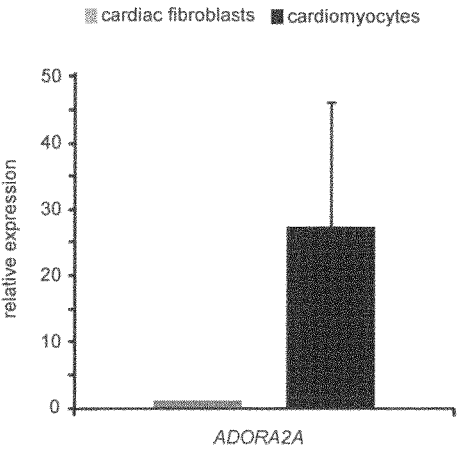

```
hadora2a    1  -XPIMGSSVYITVELAIAVLAILGNVLVCWAVWLNSNLQNVTNXFVVSLAAADIAVGVLAIPFAITISTG
madora2a    1  ----MGSSVYIMVELAIAVLAILGNVLVCWAVWXNSNLQNVTNFFVVSLAAADIAVGVLAIPFAITISTG
zadora2a    1  MXNNXFDVXYMXXELXIAXLSXLGNVLVCWAVGLNSNLQSXTNFFVVSLAXADIAVGVLAIPFSXVXSTG hadora2a   70  FCAACHGCLFIACFVLVLTQSSIFSLLAIAIDRYIAIRIPLRYNGLVTGTRAKGIIAICWVLSFAIGLTP
madora2a   67  FCAACHGCLFXACFVLVLTQSSIFSLLAIAIDRYIAIRIPLRYNGLVTGMRAKGIIAICWVLSFAIGLTP
zadora2a   71  FCANFYGCLFIACFVLVLTQSSIFSLLAIAIDRYIAIKIPLRYNSLVTGQRAXGIIAICWVLSVIIGLTP hadora2a  140  MLGWNNCGXPKEGKNHSQGCGEGQVACLFEDVVPMNYMVYFNFFACVLVPLLLMLXVYLRIFLAARRQLK
madora2a  137  MLGWNNCSQKXE--NSXKTCGEGRVTCLFEDVVPMNYMVYXNFFAFVLXPLLLMLAIYLRIFLAARRQLK
zadora2a  141  MLGWHKARLQXG---HNGTCPEGMXECLFEXVVVMDYMVYFNFFACVLVPLLLMLAIYLRIFXAARXQLK hadora2a  210  QMESQPLPGE-RARSTLQKEVHAAKSLAIIVGLFALCWLPLHIINCFTFFCPXCSHAPXWLMYLAIXLSH
madora2a  205  QMESQPLPGE-RXRSTLQKEVHAAKSLAIIVGLFALCWLPLHIINCFTFFCSTCQHAPPWLMYLAIILSH
zadora2a  208  CXESKAXECEXXRSTLQKEVHAAKSLAIIVGLFAVCWLPLHIINCFTXFCPXCERPPAIXMYLAIILSH hadora2a  279  XNSVVNPFIYAYRIREFRQTFRKIIRXHVLRQQEPFXAXGXSARVLAAHGSXGEQVSLRLNGHPPGVWAN
madora2a  274  XNSVVNPFIYAYRIREFRQTFRKIIRXHVLRRQEPFXACGSSAWALAAHSXXGEQVSLRLNGHPLGVWAN
zadora2a  278  ANSVVNPFIYAYRIREFRHTFRKIXRYHXLGRREPLSCNGSXR--TSTRXSVXXSLRIXXNGLVRELXAE hadora2a  349  GSAPHP--ERRPNGYALGLVSGG-----------SAQESQGNTGLPDVELLXHXLKGVCPXPPGLDDPLA
madora2a  344  GSAPHS--GRRPNGYTLGPGGGG-----------STQGSPG-----DVELLXQEHQ-EGQXHPGLXDXLA
zadora2a  346  QSSTTXSGESAEPGXTHRPVSTENSILDNQPIEISNSHRHTALRHPXSPLTGXNEGLACRKHAGLDITDG hadora2a  406  QDGAGVS---------------------
madora2a  395  QGRVGTASWSXEFAPS------------
zadora2a  416  KDLSSPLHIKSALYVQTAHCVELTEVS
```

EPIGENETIC SIGNATURES AS MARKER FOR CARDIOMYOPATHIES AND MYOCARDIAL INSUFFICIENCIES

CROSS REFERENCE TO A RELATED APPLICATION

This application is a National Stage Application of International Application Number PCT/EP2013/055267, filed Mar. 14, 2013; which claims the benefit of U.S. Provisional Application No. 61/610,841, filed Mar. 14, 2012; all of which are incorporated herein by reference in their entirety.

The Sequence Listing for this application is labeled "SeqList-06Sep16.txt" which was created on Sep. 6, 2016, and is 1037 KB. The entire content is incorporated herein by reference in its entirety.

The present invention relates to the use of DNA methylation profiles of patient samples for the diagnosis, prognosis and/or therapy monitoring of a heart disease in a patient, wherein the DNA methylation profile of the patient sample is compared with the DNA methylation profile of a control sample, and wherein a difference in the DNA methylation profile of the patient sample compared to the control sample is indicative of a heart disease or of the risk for developing a heart disease or for a prediction of therapy effects or therapy outcome. The present invention further relates to methods for the diagnosis, prognosis and/or therapy monitoring of a heart disease in a patient, comprising determining the DNA methylation profile in a patient sample comprising genomic DNA from heart cells, heart tissue or peripheral blood; and comparing the DNA methylation profile in the patient sample with the DNA methylation profile from a normal subject not having a heart disease or having a normal heart function. The present invention furthermore relates to kits that are suitable for the methods and uses of the invention. The present invention furthermore relates to the use of ADORA2A, ERBB3, LY75, HOXB13, GFI1, CLDN4, FDX1, ID4, NAT1, PPARGC1A, SULF2, TFF1, TKT, ATP2C, CCDC59, GSTM5m, SLC9A6 and TDG as marker for the diagnosis, prognosis and/or therapy monitoring of a heart disease in a patient.

BACKGROUND OF THE INVENTION

Cardiomyopathy is the deterioration of the function of the myocardium for any reason. People with cardiomyopathy are at risk of heart failure, arrhythmia and/or sudden cardiac death. Cardiomyopathy can often go undetected, making it especially dangerous to carriers of the disease. Cardiomyopathies can be categorized as extrinsic or intrinsic. An extrinsic cardiomyopathy is a cardiomyopathy where the primary pathology is outside the myocardium itself. Most cardiomyopathies are extrinsic, because by far the most common cause of a cardiomyopathy is ischemia. The World Health Organization calls these specific cardiomyopathies. An intrinsic cardiomyopathy is defined as weakness in the muscle of the heart that is not due to an identifiable external cause. This definition was used to categorize previously idiopathic cardiomyopathies although specific external causes have since been identified for many. The intrinsic cardiomyopathies consist of a variety of disease states, each with their own causes. Many intrinsic cardiomyopathies now have identifiable external causes including ischemia, drug and alcohol toxicity, viral infections and various genetic and idiopathic causes.

Dilated cardiomyopathy is one of the most frequent heart muscle diseases with an estimated prevalence of 1:2500. The progressive nature of this disorder is responsible for about 30-40% of all heart failure cases and is the main cause for heart transplantation in young adults. In the last decades, it was recognized that DCM has a substantial genetic contribution. It is estimated that about 30-40% of all DCM cases have a familial aggregation and until now more than 40 different genes were found to cause monogenetic DCM. However, since the course of the disease is highly variable and only a fraction of patients suffer a causal mutation, genetic modifiers are thought to play an important role (Friedrichs et al., 2009; Villard et al., 2011). Accordingly, several studies have now identified common genetic polymorphisms, which are associated with DCM or heart failure (Friedrichs et al., 2009; Villard et al., 2011). But even then, the existence of such modifiers also does not completely explain the high variability in phenotypic expression and unexplained cases of DCM.

Epigenetic mechanisms play important roles during normal development, aging and a variety of disease conditions. Numerous studies have implicated aberrant methylation in the etiology of human diseases, including cancer, MS and diabetes. Hypermethylation of CpG islands located in promoter regions of tumor suppressor genes is firmly established as the most frequent mechanism for gene activation in cancers.

Briefly, methylation of the 5' carbon of cytosine is a form of epigenetic modification that does not affect the primary DNA sequence, but affects secondary interactions that play a critical role in the regulation of gene expression. Aberrant DNA methylation may suppress transcription and subsequently gene expression.

Disease modification through epigenetic alterations has been convincingly demonstrated for different diseases (Jones and Baylin, 2002; Feinberg and Tycko, 2004). In the cardiovascular system, histone modifications and chromatin remodelling are thought to direct adaptive as well as maladaptive molecular pathways in cardiac hypertrophy and failure (Montgomery et al., 2007) and DNA methylation was found to be responsible for the hypermutability of distinct cardiac genes (Meurs and Kuan, 2011). Furthermore, recent studies have highlighted the potential interplay between environmental factors and the disease phenotype by epigenetic mechanisms (Jirtle and Skinner, 2007; Herceg and Vaissiere, 2011). However, the knowledge about the impact of epigenetic alterations on the disease phenotype in human patients is still very limited.

Thus, epigenetic mechanisms are increasingly recognized as contributors to human disease. Surprisingly, most studies conducted so far have focused on cancer and only few have investigated the role of epigenetic mechanisms, especially DNA methylation in cardiovascular disease (Movassagh et al., 2011). However, epigenetic mechanisms are thought to control key processes such as cardiac hypertrophy, fibrosis and failure (Backs et al., 2006; Backs et al., 2008).

Furthermore, the decision to initiate or escalate therapies (drugs, devices, surgical interventions) is currently based on assumptions and supported only by few diagnostic measures (Bielecka-Dabrowa et al., 2008).

There is a need for diagnostic means and methods that not only allow the detection of a heart disease but also allow to draw conclusions about the further development of an existing heart disease or whether a heart disease will develop in a patient.

SUMMARY OF THE INVENTION

According to the present invention this object is solved by the use of a DNA methylation profile of a patient sample comprising genomic DNA from heart cells, heart tissue or peripheral blood f for the diagnosis, prognosis and/or therapy monitoring of a heart disease in a patient, wherein the DNA methylation profile of the patient sample is compared with the DNA methylation profile of a control sample, and wherein a difference in the DNA methylation profile of the patient sample compared to the control sample is indicative of a heart disease or of the risk of developing a heart disease or for a prediction of therapy effects or therapy outcome.

According to the present invention this object is solved by a method f for the diagnosis, prognosis and/or therapy monitoring a heart disease in a patient, comprising
   determining the DNA methylation profile in a patient sample comprising genomic DNA from heart cells, heart tissue or peripheral blood; and
   comparing the DNA methylation profile in the patient sample with the DNA methylation profile from a normal subject not having a heart disease or having a normal heart function, wherein a difference in the DNA methylation profile is indicative of a heart disease or of the risk for developing a heart disease or for a prediction of therapy effects or therapy outcome.

According to the present invention this object is solved by providing a kit for the diagnosis, prognosis and/or therapy monitoring of a heart disease in a patient, comprising at least two sets of oligonucleotides, wherein the oligonucleotides of each set are identical, complementary or hybridize under stringent conditions to an at least 15 nucleotides long segment of a nucleic acid sequence selected from SEQ ID NOs. 1 to 18, and optionally, a reagent that distinguishes between methylated and non-methylated CpG dinucleotides.

According to the present invention this object is solved by providing at least one of ADORA2A, ERBB3, LY75, HOXB13, GFI1, CLDN4, FDX1, ID4, NAT 1, PPARGC1A, SULF2, TFF1, TKT, ATP2C, CCDC59, GSTM5m, SLC9A6 and TDG for use as a marker for the diagnosis, prognosis and/or therapy monitoring of a heart disease in a patient.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "at least 15 nucleotides, preferably 15 to 100" should be interpreted to include not only the explicitly recited values of 15 to 100, but also include individual values and sub-ranges within the indicated range. Thus, included in this numerical range are individual values such as 15, 16, 17, 18, 19, 20, 21, . . . 96, 97, 98, 99 and 100 and sub-ranges such as from 20 to 80, from 30 to 70, from 15 to 40, from 25 to 50, from 15 to 25, and from 25 to 50, etc. This same principle applies to ranges reciting only one numerical value. Furthermore, such an interpretation should apply regardless of the breadth of the range or the characteristics being described.

Use of DNA Methylation Profiles as Diagnostic, Prognostic and/or Therapeutic Marker of a Heart Disease As described above, the present invention provides the use of a DNA methylation profile of a patient sample comprising genomic DNA from heart cells, heart tissue or peripheral blood for the diagnosis, prognosis and/or therapy monitoring of a heart disease in a patient.

Thereby, the DNA methylation profile of the patient sample is compared with the DNA methylation profile of a control sample.

A difference in the DNA methylation profile of the patient sample compared to the control sample is indicative:
   of a heart disease,
   of the risk of developing a heart disease,
   of the progression or advance of a heart disease, and/or
   for a prediction of therapy effects or therapy outcome.

As used herein, providing a diagnosis of a subject/patient is determining heart failure, namely independent on the etiology of the heart failure, i.e. determining whether or not a subject has suffered heart failure recently or in the past.

As used herein, providing a prognosis of a subject t/patient is preferably selected from determining heart failure severity, risk for subsequent all-cause mortality and risk assessment of the subject with heart failure or risk for developing heart failure.

"Risk assessment" or "risk stratification" of subjects or patients with heart failure according to the present invention refers to the evaluation of factors, such as DNA methylation profiles, mutations, biomarkers, in order to predict the risk of future events or even death and in order to decide about the type, manner, dosis, regimen of therapy and treatment for the individual subject.

"Disease classification" according to the present invention refers to the severity of the specific heart failure type.

Preferably, the prognosis of a heart disease comprises risk stratification and/or disease classification.

As used herein, "therapy monitoring" or "therapy management" of a heart disease comprises treatment monitoring or treatment decision making as well as the prediction of therapy effects or therapy outcome.

The "DNA methylation profile" according to the invention is preferably
   a genome-wide DNA methylation profile,
   a whole genome cardiac DNA methylation profile The "DNA methylation profile" according to the invention preferably comprises the DNA methylation levels of CpG islands or nucleotides.

Preferably, the "DNA methylation profile" according to the invention is a genome-wide DNA methylation profile of the CpG islands or nucleotides.

The difference in the DNA methylation profile of the patient sample compared to the DNA methylation profile of the control sample is preferably
   a different degree of CpG methylation.

CpG sites or CG sites are regions of DNA where a cytosine nucleotide occurs next to a guanine nucleotide in the linear sequence of bases along its length. "CpG" is shorthand for a cytosine and a guanine separated by only one phosphate, the "CpG" notation is used to distinguish this linear sequence from the CG base-pairing of cytosine and guanine. Cytosines in CpG dinucleotides can be methylated to form 5-methylcytosine. In mammals, methylating the cytosine within a gene can turn the gene off, a mechanism that is part of a larger field of science studying gene regulation that is called epigenetics. In mammals, 70% to 80% of CpG cytosines are methylated.

There are regions of the genome that have a higher concentration of CpG sites, known as CpG islands. Many genes in mammalian genomes have CpG islands associated with the start of the gene.

A "CpG island" as used herein and according to Takai and Jones (20002) is a region with:
- a nucleotide length of at least 200 bp, or
- with a GC percentage of 50% or higher, or
- with an observed versus expected CpG ratio that is 60% or higher (where the observed/expected CpG ratio is calculated by formula: number of CpG/(number of C×number of G))×total number of nucleotides in the sequence).

CpG islands typically occur at or near the transcription start site of genes, particularly housekeeping genes, in vertebrates. Normally a C (cytosine) base followed immediately by a G (guanine) base (a CpG) is rare in vertebrate DNA because the cytosines in such an arrangement tend to be methylated. This methylation helps distinguish the newly synthesized DNA strand from the parent strand, which aids in the final stages of DNA proofreading after duplication. However, over evolutionary time methylated cytosines tend to turn into thymines because of spontaneous deamination. While there is a special enzyme in human (Thymine-DNA glycosylase, or TDG) that specifically replaces T's from T/G mismatches, it is not sufficiently effective to prevent the relatively rapid mutation of the dinucleotides. The result is that CpGs are relatively rare unless there is selective pressure to keep them or a region is not methylated for some reason, perhaps having to do with the regulation of gene expression.

Preferably, the DNA methylation profiles are determined by hybridisation-based arrays or by the use of next-generation sequencing techniques, polymerase-based as well as ligase based sequencing technologies like pyrosequencing, sequencing by ligation, single-molecule sequencing or nanopore sequencing alone or in combination with the bisulfite treatment of cytosine nucleotides.

Variation of the DNA Methylation Profiles in Time

In a preferred embodiment, the DNA methylation profile of the patient sample is determined over time.

This embodiment is preferably used for therapy monitoring or therapy management, preferably during/for long term therapy monitoring The DNA methylation profile of the patient sample is determined at different time points, during therapy.

Thereby, the DNA methylation profile is preferably determined before or at the beginning of the therapy and is then determined at different time points during the therapy.

A change in the DNA methylation profile at these different time points, when compared to the DNA methylation profile of the first measured time point, can be an indication of the progression or advance of the heart disease in the patient and/or of the success of a therapy.

Assessment of Further Biomarkers or of Mutations

In an embodiment, further biomarkers and/or genetic mutations are determined in the patient sample.

Further biomarkers are, for example, well established metabolic biomarkes, e.g. troponins or NT-proBNP, The determination of such further biomarkers and/or genetic mutations, together with the methylation profile, contributes preferably to disease risk stratification in a combinatorial manner.

The heart disease is a cardiomyopathy, myocardial insufficiency, acute or chronic heart failure, such as dilated cardiomyopathy (DCM), hypertrophic cardiomyopathy (HCM), ischemic cardiomyopathy, diastolic dysfunction, myocardial infarction.

Cardiomyopathy, which literally means "heart muscle disease", is the deterioration of the function of the myocardium for any reason. Cardiomyopathies can generally be categorized into two groups, based on WHO guidelines: extrinsic and intrinsic cardiomyopathies.

Extrinsic cardiomyopathies are cardiomyopathies where the primary pathology is outside the myocardium itself. Most cardiomyopathies are extrinsic, because by far the most common cause of a cardiomyopathy is ischemia. Ischemic cardiomyopathy, for instance, is a weakness in the muscle of the heart due to inadequate oxygen delivery to the myocardium with coronary artery disease being the most common cause.

An intrinsic cardiomyopathy is weakness in the muscle of the heart that is not due to an identifiable external cause. The term intrinsic cardiomyopathy does not describe the specific etiology of weakened heart muscle. The intrinsic cardiomyopathies are a heterogeneous group of disease states, each with their own causes. Intrinsic cardiomyopathy has a number of causes including drug and alcohol toxicity, certain infections (including hepatitis C), and various genetic and idiopathic (i.e., unknown) causes. There are four main types of intrinsic cardiomyopathy: first, dilated cardiomyopathy (DCM), the most common form, and one of the leading indications for heart transplantation. In DCM the heart (especially the left ventricle) is enlarged and the pumping function is diminished. Second, hypertrophic cardiomyopathy (HCM or HOCM), a genetic disorder caused by various mutations in genes encoding sarcomeric proteins. In HCM the heart muscle is thickened, which can obstruct blood flow and prevent the heart from functioning properly. Third, arrhythmogenic right ventricular cardiomyopathy (ARVC) arises from an electrical disturbance of the heart in which heart muscle is replaced by fibrous scar tissue. The right ventricle is generally most affected. Fourth, restrictive cardiomyopathy (RCM) is the least common cardiomyopathy. The walls of the ventricles are stiff, but may not be thickened, and resist the normal filling of the heart with blood. Furthermore, noncompaction cardiomyopathy a more recent form of cardiomyopathy is recognized as its own separate type since the 1980's. It refers to a cardiomyopathy where the left ventricle wall has failed to properly grow from birth and such has a spongy appearance when viewed during an echocardiogram.

The patient sample is preferably a sample of left ventricular tissue (such as a LV biopsy), a sample of right ventricular tissue or peripheral blood.

The control sample is preferably from a normal subject not having a heart disease or having a normal heart function, i.e. having an unaltered myocardial function.

The inventors have measured genome-wide DNA methylation profiles of (DCM) patient samples and identified candidate genes with altered methylation status that have prognostic and diagnostic value for heart diseases and are suitable for therapy monitoring as well.

In a preferred embodiment, the methylation level of at least one of the following genes is different in the patient sample compared to the control sample:

| | | Genebank Accession No. ** |
|---|---|---|
| adenosine receptor A2A (ADORA2A) | SEQ ID NO. 1 | ENSG00000128271 |
| ERBB3 | SEQ ID NO. 2 | ENSG00000065361 |
| LY75 | SEQ ID NO. 3 | ENSG00000054219 |
| HOXB13 | SEQ ID NO. 4 | ENSG00000159184 |
| GFI1 | SEQ ID NO. 5 | ENSG00000162676 |
| CLDN4 | SEQ ID NO. 6 | ENSG00000189143 |
| FDX1 | SEQ ID NO. 7 | ENSG00000137714 |
| ID4 | SEQ ID NO. 8 | ENSG00000172201 |
| NAT1 | SEQ ID NO. 9 | ENSG00000171428 |
| PPARGC1A | SEQ ID NO. 10 | ENSG00000109819 |
| SULF2 | SEQ ID NO. 11 | ENSG00000196562 |
| TFF1 | SEQ ID NO. 12 | ENSG00000160182 |
| TKT | SEQ ID NO. 13 | ENSG00000163931 |
| ATP2C | SEQ ID NO. 14 | ENSG00000017260 |
| CCDC59 | SEQ ID NO. 15 | ENSG00000133773 |
| GSTM5m | SEQ ID NO. 16 | ENSG00000134201 |
| SLC9A6 | SEQ ID NO. 17 | ENSG00000198689 |
| TDG | SEQ ID NO. 18 | ENSG00000139372 |

** Ensembl Genebank (see www.ensembl.org)

All listed identifier and gene names and the corresponding gene sequences and gene related sequences like transcript and protein sequences were retrieved from the Ensembl database (http://www.ensembl.org) release 70 from January 2013. Which relates to either GRCh37.p10 (human) or Zv9 (zebrafish). The mentioned resources have also been used for primer design.

More preferably, the methylation level of at least one of ADORA2A, ERBB3 and LY75 is different in the patient sample compared to the control sample.

More preferably, the methylation level of at least one of LY75, ADORA2A, ERBB3 and HOXB13 is different in the patient sample compared to the control sample.

More preferably, the methylation level of at least one of LY75, ADORA2A, ERBB3, HOXB13 and GFI1 is different in the patient sample compared to the control sample Preferably, the methylation level of at least one of ADORA2A, ERBB3, HOXB13, CLDN4, FDX1, ID4, NAT1, PPARGC1A, SULF2, TFF1 and TKT (SEQ ID NOs. 1, 2, 4, 6-13) is reduced in the patient sample compared to the control sample (hypo-methylation), more preferably of at least one of ADORA2A, ERBB3, HOXB13.

Preferably, the methylation level of at least one of LY75, GFI1, ATP2C, CCDC59, GSTM5m, SLC9A6 and TDG (SEQ ID NOs. 3, 5, 14-18) is higher in the patient sample compared to the control sample (hyper-methylation), more preferably of LY75.

LY75 is a collagen-binding mannose family receptor that is transcriptionally controlled by the Interleukin-6 receptor IL6Rα (Giridhar et al., 2011). For LY75, the dys-methylated CpGs reside within a classical CpG island covering Exon 1 as well as part of the 5' upstream region. Its transcriptional start-site is predicted in very close vicinity (1,395 bp). Our findings of a significantly increased DNA methylation together with strongly reduced LY75-mRNA levels in DCM patients suggested a functional role. While it is to our knowledge not possible to recreate exactly the same methylation patterns in vitro as seen in the primary tissue, we could investigate here the functional consequence of global LY75 promoter methylation, suggesting a direct link between methylation and transcriptional activity. We also knocked down ly75 in the zebrafish model and find not only cardiac dysfunction in ly75-ablated embryos, but also a noticeable skin detachment phenotype, potentially due to disturbed collagen production.

The adenosine receptor A2A (ADORA2A) is a member of the G protein-coupled receptor family and is highly abundant in neurons of basal ganglia, T lymphocytes, platelets, and vasculature, but also shows relevant expression in myocardium as shown herein. In the heart, activation of ADORA2A enhances cAMP production through αGs proteins (Sommerschild et al., 2000) and overexpression results in increased contractility and sarcoplasmic reticulum $Ca^{2+}$ uptake (Hamad et al., 2010) as well as cardio protection in ischemia and reperfusion damage (Urmaliya et al., 2009). Surprisingly, although ADORA2A methylation is reduced, we find mRNA levels to be significantly down-regulated. Hence, hyper-methylation can sometimes result in increased gene expression as observed in the case of ADORA2A. Our CGI annotation was based on the criteria by Takai and Jones (2002), which define a CpG island as a nucleotide sequence of 200 bp or greater in length or with a GC content of 50% or more, or a ratio of observed versus expected CpGs of 0.6 or higher. In case of ADORA2A, the tested CGIs only met the second criterion and may therefore not be classical CGIs.

The receptor tyrosine-protein kinase ERBB3 belongs to the membrane bound epidermal growth factor receptor (EGFR) family. Functionally it is implicated in SOX10 mediated neural crest and early heart development (Erickson et al., 1997). However, since knock-out of ERBB3 leads to early embryonic lethality, its role in regulation of cardiac contractility was previously unknown. In the present invention, the inventors used the zebrafish as animal model for investigating the functional role of ERBB3. Knock-down of erbb3b results in a similar, but earlier phenotype as adora2a. Additionally, erbb3b-morphants show regurgitation of blood into the ventricle, suggesting impaired cardiac valve development. cDNA splice-site analysis revealed a completely insertion of intron 2 as well a partial exclusion exon 2 producing an aberrant, frameshifted transcripts with premature termination codons.

The HOXB13 gene is a member of the homeobox gene family and is encoding a transcription factor. The homeobox gene family clusters on chromosome 17 in the 17qw21-22 region and is highly conserved and essential for vertebrate development.

Methods for the Diagnosis, Prognosis and/or Therapy Monitoring of a Heart Disease in a Patient As described above, the present invention provides a method for the diagnosis, prognosis and/or therapy monitoring of a heart disease in a patient.

The method comprises
  determining the DNA methylation profile in a patient sample comprising genomic DNA from heart cells, heart tissue or peripheral blood; and
  comparing the DNA methylation profile in the patient sample with the DNA methylation profile from a normal subject not having a heart disease or having a normal heart function.

As described above, a difference in the DNA methylation profile of the patient sample compared to the control sample is indicative:
  of a heart disease,
  of the risk of developing a heart disease, and/or
  for a prediction of therapy effects or therapy outcome.
The method furthermore preferably comprising the step of
  contacting genomic DNA isolated from the patient sample with at least one reagent that distinguishes between methylated and non-methylated CpG dinucleotides.

Reagents that distinguish between methylated and non-methylated CpG dinucleotides are known in the art, such as bisulfite, hydrogen sulfite, disulfite, and combinations thereof.

In a preferred embodiment, the DNA methylation profile of the patient sample is determined over time at different time points, preferably during therapy monitoring, as described above.

Preferably, the DNA methylation profiles are determined by hybridisation-based arrays or by the use of next-generation sequencing techniques, polymerase-based as well as ligase based sequencing technologies like pyrosequencing, sequencing by ligation, single-molecule sequencing or nanopore sequencing alone or in combination with the bisulfite conversion/treatment of cytosine nucleotides.

As described above, the heart disease is a cardiomyopathy, myocardial insufficiency, acute or chronic heart failure, such as dilated cardiomyopathy (DCM), hypertrophic cardiomyopathy (HCM), ischemic cardiomyopathy, diastolic dysfunction, myocardial infarction.

The patient sample is preferably a sample of left ventricular tissue (such as a LV biopsy), a sample of right ventricular tissue or peripheral blood.

The control sample is preferably from a normal subject not having a heart disease or having a normal heart function, i.e. having an unaltered myocardial function.

As described above, the prognosis of a heart disease preferably comprises risk stratification and/or disease classification.

As described above, the therapy monitoring of a heart disease preferably comprises treatment monitoring or treatment decision making as well as the prediction of therapy effects or therapy outcome.

The inventors have measured genome-wide DNA methylation profiles of (DCM) patient samples and identified candidate genes with altered methylation status that have prognostic and diagnostic for heart diseases and are suitable for therapy monitoring as well.

In a preferred embodiment, the methylation level of at least one of the following genes is different in the patient sample compared to the control sample:

|   |   | Genebank Accession No. ** |
|---|---|---|
| adenosine receptor A2A (ADORA2A) | SEQ ID NO. 1 | ENSG00000128271 |
| ERBB3 | SEQ ID NO. 2 | ENSG00000065361 |
| LY75 | SEQ ID NO. 3 | ENSG00000054219 |
| HOXB13 | SEQ ID NO. 4 | ENSG00000159184 |
| GFI1 | SEQ ID NO. 5 | ENSG00000162676 |
| CLDN4 | SEQ ID NO. 6 | ENSG00000189143 |
| FDX1 | SEQ ID NO. 7 | ENSG00000137714 |
| ID4 | SEQ ID NO. 8 | ENSG00000172201 |
| NAT1 | SEQ ID NO. 9 | ENSG00000171428 |
| PPARGC1A | SEQ ID NO. 10 | ENSG00000109819 |
| SULF2 | SEQ ID NO. 11 | ENSG00000196562 |
| TFF1 | SEQ ID NO. 12 | ENSG00000160182 |
| TKT | SEQ ID NO. 13 | ENSG00000163931 |
| ATP2C | SEQ ID NO. 14 | ENSG00000017260 |
| CCDC59 | SEQ ID NO. 15 | ENSG00000133773 |
| GSTM5m | SEQ ID NO. 16 | ENSG00000134201 |
| SLC9A6 | SEQ ID NO. 17 | ENSG00000198689 |
| TDG | SEQ ID NO. 18 | ENSG00000139372 |

** Ensembl Genebank (see www.ensembl.org)

All listed identifier and gene names and the corresponding gene sequences and gene related sequences like transcript and protein sequences were retrieved from the Ensembl database (http://www.ensembl.org) release 70 from January 2013. Which relates to either GRCh37.p10 (human) or Zv9 (zebrafish). The mentioned resources have also been used for primer design.

More preferably, the methylation level of at least one of ADORA2A, ERBB3 and LY75 is different in the patient sample compared to the control sample.

More preferably, the methylation level of at least one of ADORA2A, ERBB3, HOXB13 and LY75 is different in the patient sample compared to the control sample.

More preferably, the methylation level of at least one of LY75, ADORA2A, ERBB3 and HOXB13 is different in the patient sample compared to the control sample.

More preferably, the methylation level of at least one of LY75, ADORA2A, ERBB3, HOXB13 and GFI1 is different in the patient sample compared to the control sample Preferably, the methylation level of at least one of ADORA2A, ERBB3, HOXB13, CLDN4, FDX1, ID4, NAT1, PPARGC1A, SULF2, TFF1 and TKT (SEQ ID NOs. 1, 2, 4, 6-13) is reduced in the patient sample compared to the control sample (hypo-methylation), more preferably at least one of ADORA2A, ERBB3, HOXB13.

Preferably, the methylation level of at least one of LY75, GFI1, ATP2C, CCDC59, GSTM5m, SLC9A6 and TDG (SEQ ID NOs. 3, 5, 14-18) is higher in the patient sample compared to the control sample (hyper-methylation), more preferably of LY75.

Kits for the Diagnosis, Prognosis and/or Therapy Monitoring of a Heart Disease in a Patient As described above, the present invention provides a kit for the diagnosis, prognosis and/or therapy monitoring of a heart disease in a patient.

The kit comprises at least two sets of oligonucleotides, wherein the oligonucleotides of each set are identical, complementary or hybridize under stringent conditions to an at least 15 nucleotides long segment of a nucleic acid sequence selected from SEQ ID NOs. 1 to 18, preferably 15 to 100 nucleotides long segment of a nucleic acid sequence selected from SEQ ID NOs. 1 to 18, such as 20 to 80 or 30 to 70, such as about 25 nucleotides.

The kit optionally comprises a reagent that distinguishes between methylated and non-methylated CpG dinucleotides.

The kit is preferably suitable for the use of/with/in hybridisation-based arrays or next-generation sequencing techniques, polymerase-based as well as ligase based sequencing technologies, like pyrosequencing, sequencing by ligation, single-molecule sequencing or nanopore sequencing alone or in combination with the bisulfite treatment/conversion of cytosine nucleotides.

Thus, the kit comprises at least two sets of oligonucleotides for the detection of two target nucleic acids/genes (selected from SEQ ID NOs. 1 to 18).

Reagents that distinguish between methylated and non-methylated CpG dinucleotides are known in the art, such as bisulfite, hydrogen sulfite, disulfite, and combinations thereof.

As described above, the prognosis of a heart disease preferably comprises risk stratification and/or disease classification.

As described above, the therapy monitoring of a heart disease preferably comprises treatment monitoring or treatment decision making as well as the prediction of therapy effects or therapy outcome.

Markers for Heart Diseases

As described above, the present invention provides the use of at least one of ADORA2A, ERBB3, LY75, HOXB13, GFI1, CLDN4, FDX1, ID4, NAT1, PPARGC1A, SULF2, TFF1, TKT, ATP2C, CCDC59, GSTM5m, SLC9A6 and TDG as marker for the diagnosis, prognosis and/or therapy monitoring of a heart disease in a patient.

|  |  | Genebank Accession No. ** |
|---|---|---|
| adenosine receptor A2A (ADORA2A) | SEQ ID NO. 1 | ENSG00000128271 |
| ERBB3 | SEQ ID NO. 2 | ENSG00000065361 |
| LY75 | SEQ ID NO. 3 | ENSG00000054219 |
| HOXB13 | SEQ ID NO. 4 | ENSG00000159184 |
| GFI1 | SEQ ID NO. 5 | ENSG00000162676 |
| CLDN4 | SEQ ID NO. 6 | ENSG00000189143 |
| FDX1 | SEQ ID NO. 7 | ENSG00000137714 |
| ID4 | SEQ ID NO. 8 | ENSG00000172201 |
| NAT1 | SEQ ID NO. 9 | ENSG00000171428 |
| PPARGC1A | SEQ ID NO. 10 | ENSG00000109819 |
| SULF2 | SEQ ID NO. 11 | ENSG00000196562 |
| TFF1 | SEQ ID NO. 12 | ENSG00000160182 |
| TKT | SEQ ID NO. 13 | ENSG00000163931 |
| ATP2C | SEQ ID NO. 14 | ENSG00000017260 |
| CCDC59 | SEQ ID NO. 15 | ENSG00000133773 |
| GSTM5m | SEQ ID NO. 16 | ENSG00000134201 |
| SLC9A6 | SEQ ID NO. 17 | ENSG00000198689 |
| TDG | SEQ ID NO. 18 | ENSG00000139372 |

** Ensembl Genebank (see www.ensembl.org)

All listed identifier and gene names and the corresponding gene sequences and gene related sequences like transcript and protein sequences were retrieved from the Ensembl database (http://www.ensembl.org) release 70 from January 2013. Which relates to either GRCh37.p10 (human) or Zv9 (zebrafish). The mentioned resources have also been used for primer design.

In a preferred embodiment at least one of ADORA2A, ERBB3 and LY75 are used as such a marker.

In a preferred embodiment at least one of LY75, ADORA2A, ERBB3 and HOXB13 are used as such a marker.

In a preferred embodiment at least one of LY75, ADORA2A, ERBB3, HOXB13 and GFI1 are used as such a marker.

Preferably, the use of said (target) genes, nucleic acids or polypeptides encoded by the genes/nucleus acids as biomarkers comprises determining the methylation level of at least one of SEQ ID NOs. 1-18 in a patient sample comprising genomic DNA from heart cells, heart tissue or peripheral blood; and comparing it with the methylation level from a normal subject not having a heart disease, wherein, and as described above, a difference in the DNA methylation profile is indicative of a heart disease or of the risk for developing a heart disease or for a prediction of therapy effects or therapy outcome.

Preferably, and as described above, the heart disease is a cardiomyopathy, myocardial insufficiency, heart failure (acute or chronic),
such as DCM dilated cardiomyopathy (DCM), hypertrophic cardiomyopathy (HCM), ischemic cardiomyopathy, diastolic dysfunction, myocardial infarction.

Preferably, and as described above, the patient sample is a sample of left ventricular tissue, right ventricular tissue or peripheral blood.

Preferably, and as described above, the control sample is from a normal subject not having a heart disease or having a normal heart function.

As described above, the prognosis of a heart disease preferably comprises risk stratification and/or disease classification.

As described above, the therapy monitoring of a heart disease preferably comprises treatment monitoring or treatment decision making as well as the prediction of therapy effects or therapy outcome.

Further Description of the Invention

Summary

Problem: Dilated cardiomyopathy (DCM) is one the most frequent heart muscle diseases. Although several factors including genetic mechanisms are found to cause DCM, we still find many cases unexplained and observe a high phenotypic variability with respect to disease severity and prognosis. Epigenetic mechanisms are increasingly recognized as causes and modulators of human disease. Therefore, we studied genome-wide cardiac DNA methylation in DCM patients and controls to detect a possible epigenetic contribution to DCM.

Results: We detected distinct DNA methylation patterns in left ventricular heart tissue of DCM patients and replicated the epigenetic mode of regulation for several genes with previously unknown function in DCM, namely Lymphocyte antigen 75 (LY75), Tyrosine kinase-type cell surface receptor HER3 (ERBB3), Homeobox B13 (HOXB13), and Adenosine receptor A2A (ADORA2A). The results were carefully verified by alternative techniques in a well phenotyped and large independent cohort of DCM patients and controls. Furthermore, we are able to show the functional relevance for the contribution of the identified genes in the pathogenesis of heart failure by using the zebrafish as an in vivo model.

Impact: Our results hint at a novel layer in the pathogenesis of DCM and heart failure and have an impact on the development of novel biomarkers and future therapeutic strategies.

Discussion

In the present study, genome-wide cardiac DNA methylation was examined for the first time in patients with idiopathic DCM and controls. We detected methylation differences in pathways related to heart disease, but also in genes with yet unknown function in DCM or heart failure, namely Lymphocyte antigen 75 (LY75), Tyrosine kinase-type cell surface receptor HER3 (ERBB3), Homeobox B13 (HOXB13), and Adenosine receptor A2A (ADORA2A). Mass-spectrometric analysis and bisulfate-sequencing enabled confirmation of the observed DNA methylation changes in independent cohorts. Aberrant DNA methylation in DCM patients was associated with significant changes in LY75 and ADORA2A mRNA expression, but not in ERBB3 and HOXB13. By in vivo studies of orthologous ly75 and adora2a in zebrafish, we could demonstrate for the first time a functional role of these genes in adaptive or maladaptive pathways in heart failure.

In detail, we investigated here DNA methylation patterns on a genome-wide level in myocardium from patients with idiopathic DCM and functionally unaffected hearts of patients who had received heart transplantation. We found and confirmed aberrant DNA methylation alterations in a number of CGIs, suggesting that DNA methylation is associated with cardiac function and may modulate phenotypic characteristics of idiopathic DCM.

Recently, Movassagh et al. (2011) reported distinct epigenomic features in explanted human failing hearts, highlighting a potential role of DNA methylation also in end-stage heart failure. However, feasibility of the used methyl-DNA precipitation and sequencing is restricted by the relatively large amounts of required tissue, which is not easily available from living patients.

Furthermore, handling of the tissue and time points of DNA isolation were quite different in controls and patients. Tissue specimens from explanted hearts of end-stage heart failure patients may be altered due to tissue handling and could have undergone secondary alterations because of degradation, missing oxygenation, innervation, and arrest of pumping function (Talens et al., 2010). Also, the authors did not replicate their findings, which were obtained in 4 patients, in an independent series of unrelated samples and by an alternative methodology. Therefore, we used a different approach, confirmed our findings in a large replication cohort with two alternative methodologies and applied functional studies to underscore the relevance of our results.

Since availability of appropriate myocardial tissue from living patients is limited, studies on epigenetic alterations in patients with heart disease are rare. As a primary referral center for cardiomyopathies, we could enroll a high number of patients and controls in this study. Our controls are not completely healthy, but had previously received heart transplantation. Hence, potential confounders include patient's medication and medical history. Importantly, on the functional level all controls had an unconstrained cardiac function as a prerequisite and we could apply the exactly same standardized procedure to sample and process left ventricular biopsies from DCM patients and controls. However, all controls received immunosuppressive medications to prevent organ rejection. This medication might influence on at least some genes. As shown herein, we found unchanged methylation levels for the tested genes in control subjects before and after heart transplantation, showing that immunosuppressives do not, at least in whole peripheral blood, impact on CGI DNA methylation of LY75, ADORA2A, ERBB3 and HOXB13.

Tissue samples are composed of different cell types, which might change during disease progression. In the present study, we have paid special attention to patient selection and the process of tissue sampling. Consequently, this resulted in high homogeneity of overall methylation patterns as shown above. In a study by Grzeskowiak et. al (2003) it was demonstrated that differences in gene expression of LV myocardial biopsies from controls and idiopathic DCM patients are almost exclusively due to genes expressed in cardiomyocytes and that the contribution of the second most common cell type, fibroblasts, is rather low and mostly unchanged during DCM. The increased fibrosis observed in human DCM, for instance, seems to be mainly due to extracellular collagen deposition rather than an increase of cardiofibroblasts. Our in vivo experiments clearly underline that reduced expression of LY75 and ADORA2A in cardiomyocytes leads to heart failure as observed in our patients. Together, this approach allowed us to study epigenetic mechanisms and its functional consequences without the confounding background of organ hypoxia and apoptosis in explanted hearts of deceased patients.

In a funnel approach, we first investigated global methylation patterns and found that methylation patterns also reflect cardiac disease pathways. Our global methylation analyses identified cardiac disease pathways and were complemented by extensive validation studies applying the highly precise MassARRAY and bisulfite sequencing techniques. We found 12 of 20 genes showing the same direction of dys-methylation as found in the screening stage, and four reached statistical significance. This has at least three reasons: 1) we expected a high false positive rate due to the relatively small screening cohorts in contrast to the number of measured epigenetic features, 2) we performed the replication measurements with a completely independent methodology, and 3) we carried out these analyses in independent patients and controls. Therefore, the genes identified here represent consistently validated targets that show an epigenetic mode of regulation.

The deciphering of the functional implications of changes in DNA methylation is difficult but of pivotal importance. Since in many cases changes in CpG methylation are correlated to the accessibility of DNA to transcription factors and polymerases, measurements of mRNA levels represent an appropriate methodology. In the present study, we find that methylation of novel cardiac genes is altered in patients with DCM. Hence, it can be hypothesized that the dys-methylated and dys-regulated genes also exert a functional role in the heart.

The receptor tyrosine-protein kinase ERBB3 belongs to the membrane bound epidermal growth factor receptor (EGFR) family. Functionally it is implicated in SOX10 mediated neural crest and early heart development (Erickson et al., 1997). However, since knock-out of ERBB3 leads to early embryonic lethality, its role in regulation of cardiac contractility was previously unknown. Although we could not observe changes in ERBB3 transcript levels, the significant changes in DNA methylation could be a susceptibility factor mediated through yet unknown pathways, e.g. by exerting effects on DNA stability, ERBB3 isoform expression, or Histon binding.

LY75, a collagen-binding mannose family receptor, is transcriptionally controlled by the Interleukin-6 receptor IL6Rα (Giridhar et al., 2011) and mediates antigen uptake and presentation in a Clathrin-dependent manner. For DCM, a correlation of IL-6 levels and cross-linked type I collagen was found, potentially implicating a role of IL-6/LY75 signaling in cardiac remodeling (Timonen et al., 2008). For LY75, the dys-methylated CpGs reside within a classical CpG island covering Exon 1 as well as part of the 5' upstream region. Its transcriptional start-site is predicted in very close vicinity (1,395 bp). Our findings of a significantly increased DNA methylation together with strongly reduced LY75-mRNA levels in DCM patients suggested a functional role. While it is to our knowledge not possible to recreate exactly the same methylation patterns in vitro as seen in the primary tissue, we could investigate here the functional consequence of global LY75 promoter methylation, suggesting a direct link between methylation and transcriptional activity. We also knocked down ly75 in the zebrafish model and find not only cardiac dysfunction in ly75-ablated embryos, but also a noticeable skin detachment phenotype, potentially due to disturbed collagen production.

The adenosine receptor A2A (ADORA2A) is a member of the G protein-coupled receptor family and is highly abundant in neurons of basal ganglia, T lymphocytes, platelets, and vasculature, but also shows relevant expression in myocardium as shown herein. In the heart, activation of ADORA2A enhances cAMP production through αGs proteins (Sommerschild et al., 2000) and overexpression results in increased contractility and sarcoplasmic reticulum $Ca^{2+}$ uptake (Hamad et al., 2010) as well as cardio protection in ischemia and reperfusion damage (Urmaliya et al., 2009). Surprisingly, although ADORA2A methylation is reduced, we find mRNA levels to be significantly down-regulated. Such a positive relationship was described for other genes and is not fully understood in each case (Zhang et al., 2006). Our CGI annotation was based on the criteria by Takai and Jones (2002), which define a CpG island as a nucleotide sequence of 200 bp or greater in length or with a GC content of 50% or more, or a ratio of observed versus expected CpGs of 0.6 or higher. In case of ADORA2A, the tested CGIs only met the second criterion and may therefore not be classical CGIs.

For such sites, one explanation can be that hyper-methylation cannot only impede the binding of transcriptional activators but also can affect repressors of transcription. We therefore performed an in silico analysis of the promoter region of ADORA2A and found two binding-sites of the transcription factor CTCF (CCCTC-binding factor) in close vicinity to both significantly hypo-methylated CGIs, but not within the single unaffected CGI of ADORA2A. CTCF is a unique insulator-binding protein, which can act as transcriptional repressor by blocking distinct enhancer regions (Bell et al., 1999; Gaszner and Felsenfield, 2006). Intriguingly, CTCF sites emerge as central players in regulatory networks linking gene regulation with epigenetic modifications (Bell and Felsenfield, 2000). Accordingly, our observed decrease in ADORA2A expression might be a result of enhanced binding of CTCF-repressors due to CGI hypomethylation. One explanation is that hyper-methylation cannot only silence the binding of transcriptional activators, but also affect repressors of transcription. Hence, hyper-methylation can sometimes result in increased gene expression as observed in the case of ADORA2A.

The detection of epigenetic mechanisms in human heart disease represents an attractive option to identify and dissect and later in target completely novel pathomechanisms. Hence, the validated targets from this study that have shown functional relevance are most likely modifiers of DCM rather than being independent disease causes and can, thus, can be further investigated for their diagnostic and therapeutic potential. Therefore, it is reasonable to investigate their potential as diagnostic and therapeutic targets specifically in DCM but also in heart failure due to other causes. In the cancer field, epigenetic drugs have already entered the clinical arena (e.g. Decitabine or Azacitidine in the treatment of myelodysplastic syndromes), and methylation patterns are used as biomarkers to subtype and stage various cancers as a critical step towards a more effective personalized care (Coppede 2011; Litzow 2011). Hence, the genes identified here are relevant druggable targets in DCM and heart failure and aid in disease classification or risk stratification.

The following examples and drawings illustrate the present invention without, however, limiting the same thereto.

A) Correlation plot showing the percentage of CpG methylation in controls versus DCM patients resulting in an overall very high correlation. Overall, correlation between both cohorts is high, however some outliers show hyper- or hypo-methylation in cases.

B) Gene-Set Enrichment Analysis for NIA human disease pathways. The area proportional Venn diagram shows that methylation changes in cardiovascular disease genes are significantly enriched together with the overlap of the other indicated gene sets.

C) Cluster analysis for genes with known expression in the human heart and significantly altered methylation. The color code used for the heatmap is shown in the upper left corner, values range from 1 (sample with the lowest methylation for the considered gene) to 17 (sample with the highest methylation for the considered genes). Genes with higher methylation found in controls cluster in the upper right quarter. Genes with higher methylation in DCM gather in the lower left quarter. Hypomethylation is shown for genes clustering in the upper left quarter for DCM and lower right quarter for controls.

Figure 2:
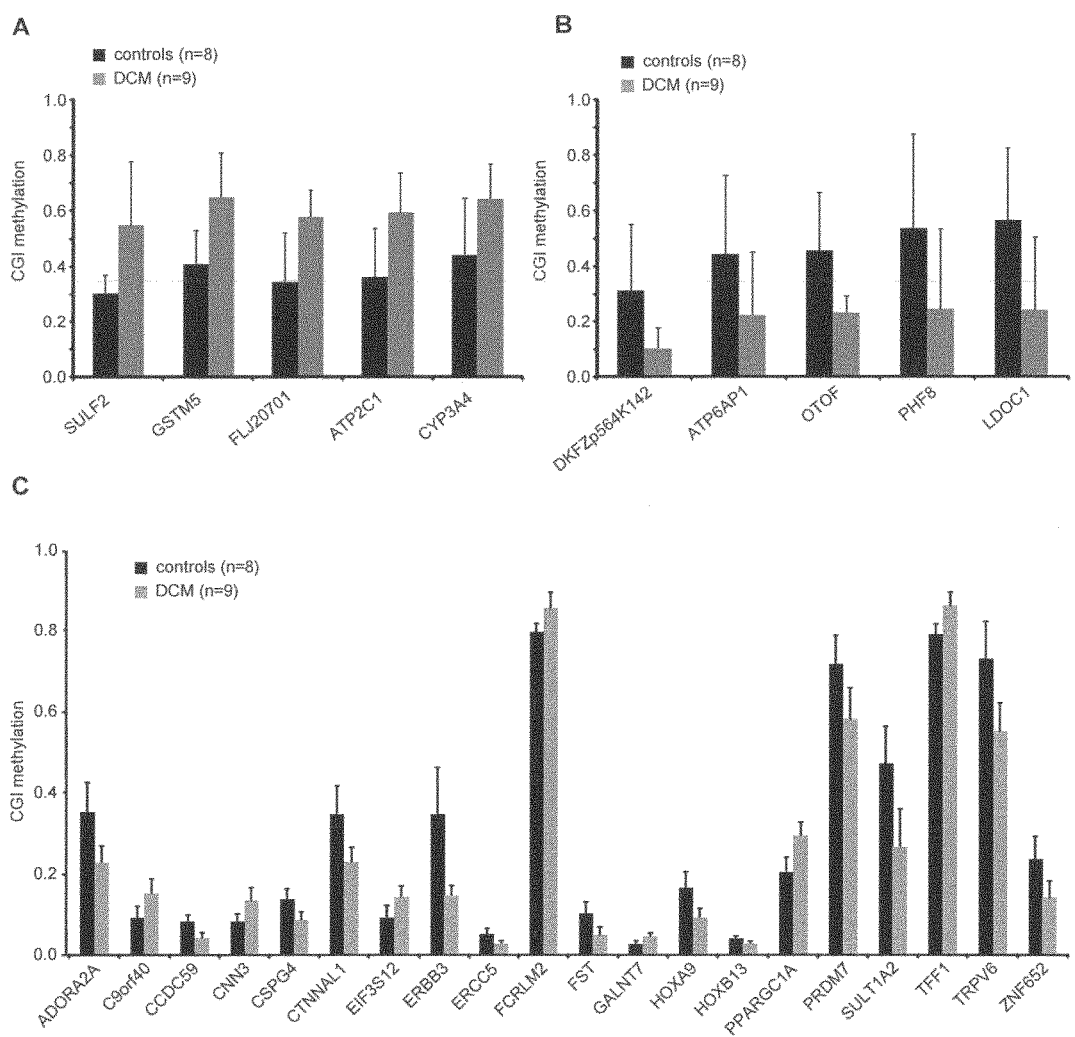

FIG. 2 Differentially methylated genes in DCM patients.

A-C) Bar graphs showing the degree of methylation of CGIs of the screening cohort (n=9 DCM patients; n=8 controls). The 5 genes with the largest increase in methylation in DCM patients are shown in A) and genes with the largest decrease in methylation are displayed in B). C) Shown are the 20 genes with the most significant methylation changes in the screening phase. Error bars indicating standard deviation.

Figure 3:
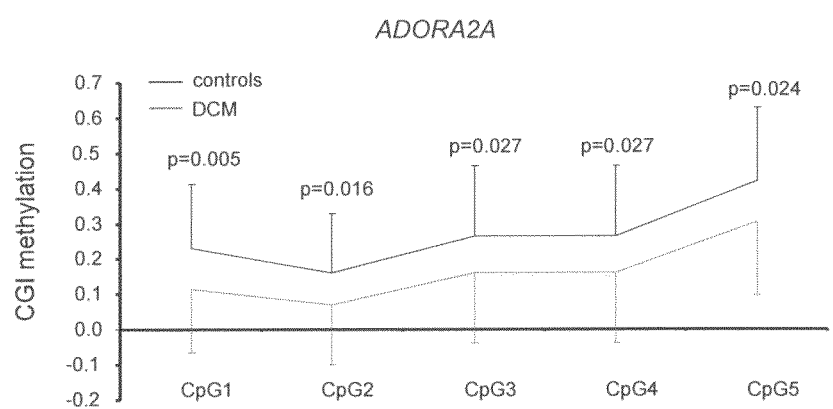

FIG. 3 MassARRAY-based validation of dys-methylated genes.

A and B) MassARRAY-based validation of differential methylation in LY75 and ERBB3. DCM patients show significantly increased DNA methylation in LY75 (A), while ERBB3 is significantly lower methylated (B). The schemes above the methylation graphs represent the tested CGIs (CGI-1, CGI-2, CGI-3), in relation to the predicted transcription start-site (leftmost vertical line), the exons (black bars) and alternatively spliced exons (white boxes) of the genes. A) The box and whiskers plot (min to max) on the upper left side represents the mean CpG methylation measured by MassARRAY, the individual CpG methylation is shown at the bottom. The pattern of CpG methylation in multiple clones is shown on the upper right insert. B) The box and whiskers plot (min to max) on the left side represents the mean CpG methylation measured by MassARRAY, the individual CpG methylation is shown on the right.

C and D) MassARRAY-based validation of differential methylation in HOXB13 and ADORA2A.

DCM patients show significantly decreased DNA methylation in HOXB13 (A) and ADORA2A (B). A) The box and whiskers plot (min to max) on the left side represents the mean CpG methylation measured by MassARRAY, the individual CpG methylation is shown on the right. B) The scheme above the graph represents the tested CGI, in relation to the predicted transcription start site (leftmost vertical line), the exons (black boxes) and alternatively spliced exons (white boxes) of adora2a. Dashed lines indicate the 1500 bp up- and downstream region of the CGIs wherein the listed transcription factor binding sites are found. Boxplots below show the mean methylation in DCM and controls at the corresponding CGI. The pattern of CpG methylation as assessed by bisulfite-sequencing in multiple clones is shown for CGI-1 at the bottom of the figure.

(E) MassARRAY-based validation of differential methylation in ADORA2A. Graph representing individual CpG methylation in ADORA2A measured by MassARRAY in DCM patients and controls.

FIG. 4 MassARRAY-based validation of further dys-methylated genes.

Graphs representing the mean CGI methylation of targets included in the replication stage. DCM patients show a reduction in methylation level in CLDN4, FDX1, ID4, NAT1, PPARGC1A, SULF2, TFF1, TKT, FLJ20701 and an increase of methylation in ATP2C, CCDC59, GFI1, GSTM5m, SLC9A6, and TDG.

Figure 5:
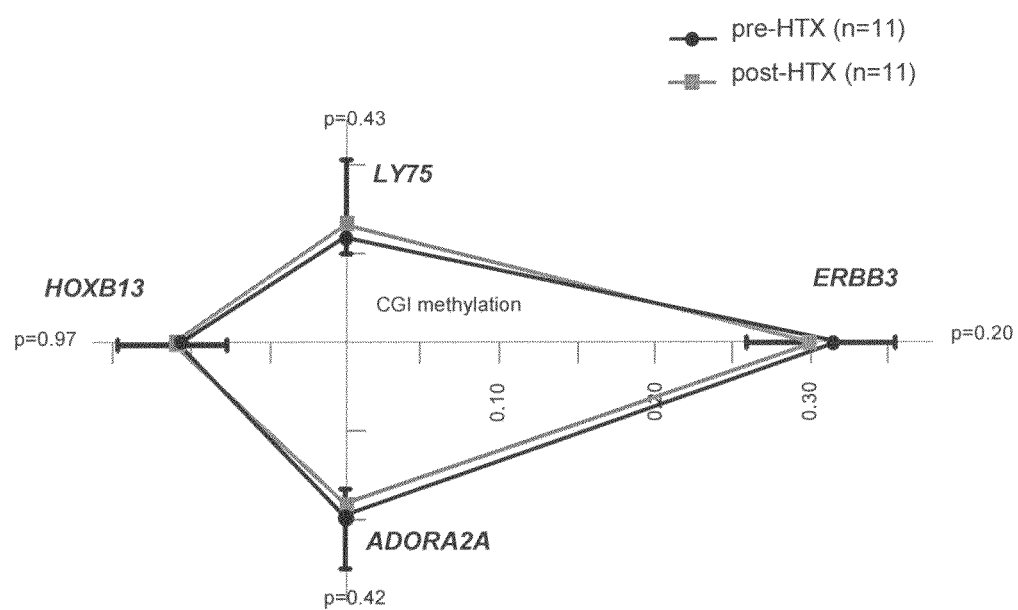

FIG. 5 CpG island methylation of control subjects before and after heart transplantation.

The line diagram shows the highly similar degree of methylation of DNA derived from peripheral blood of control subjects pre- (circlescattered line) and post- (squaresscattered line) heart transplantation (n=11) for LY75, ADORA2A, ERBB3 and HOXB13. Error bars indicating standard deviation.

FIG. 6 mRNA Expression of genes with altered methylation status and gene promoter analysis.

A-C) Bar graphs showing relative mRNA expression levels of LY75, ERBB3 and ADORA2A in mild and moderate-severe DCM in comparison to controls. A) LY75 expression is strongly reduced (relative expression=0.04), while ERBB3 (B) mRNA levels are not differentially regulated. C) ADORA2A is also significantly down-regulated in DCM (relative expression=0.37).

D) Given are the mean delta-CT values (±SEM) of LY75, ERBB3, and ADORA2A in the different groups (controls, moderate DCM, severe DCM). The reference is based on the mean of the three housekeeper genes: GAPDH, RPL13, β-Actin.

E) Left: Schema of the vector construct to measure LY75 promoter activity without and after treatment with the methylase SssI. Right: Relative promoter activity (mean of 3 technical replicates±SD) showing the strongly reduced activity in LY75 after methylation, whereas the negative control does not show significant differences.

FIG. 7 ly75 and adora2a tissue and cell-type expression.

A) Relative expression levels of ly75 and adora2a quantified by q-PCR in 40 whole zebrafish embryos (grey bars) and 200 isolated zebrafish embryonic hearts (black bars). B-C) Expression of ly75 and adora2a in neonatal rat cardiomyocytes and cardiofibroblasts (n=3 biological replicates). Error bars indicating standard deviation.

Figure 8:
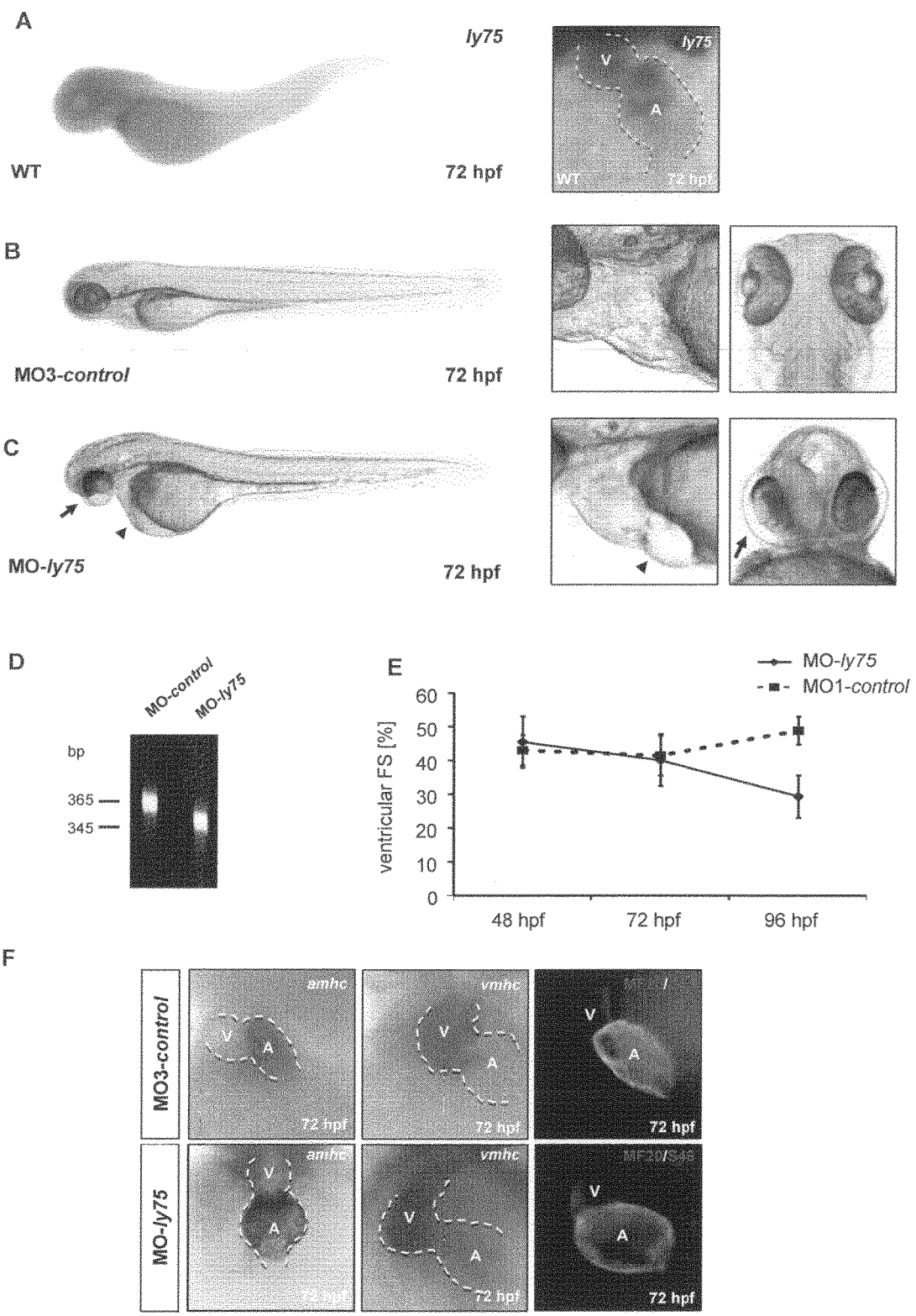

FIG. 8 ly75 is essential to maintain cardiac contractility.

A) mRNA antisense in situ hybridization showing that ly75 is significantly expressed in the zebrafish heart. B, C) Lateral views of MO3-control (B) and MO-ly75 (C) injected embryos at 72 hpf. After depletion of ly75, which can be monitored by cDNA splice-analysis (D), zebrafish hearts show reduced contractile force (E) and precardial blood congestion (arrowhead) as sign of manifest heart failure. Ly75-morphants also show noticeable skin detachment most pronounced in the head/eye region (C).

F) Molecular chamber definition is not impaired in ly75-morphants compared to the control-injected zebrafish as demonstrated by regular amhc, vmhc, MF20, and S46 expression. hpf=hours post fertilization; amhc=atrial myosin heavy-chain; vmhc=ventricular myosin heavy-chain; A=atrium; V=ventricle. Error bars indicating standard deviation.

Figure 9:
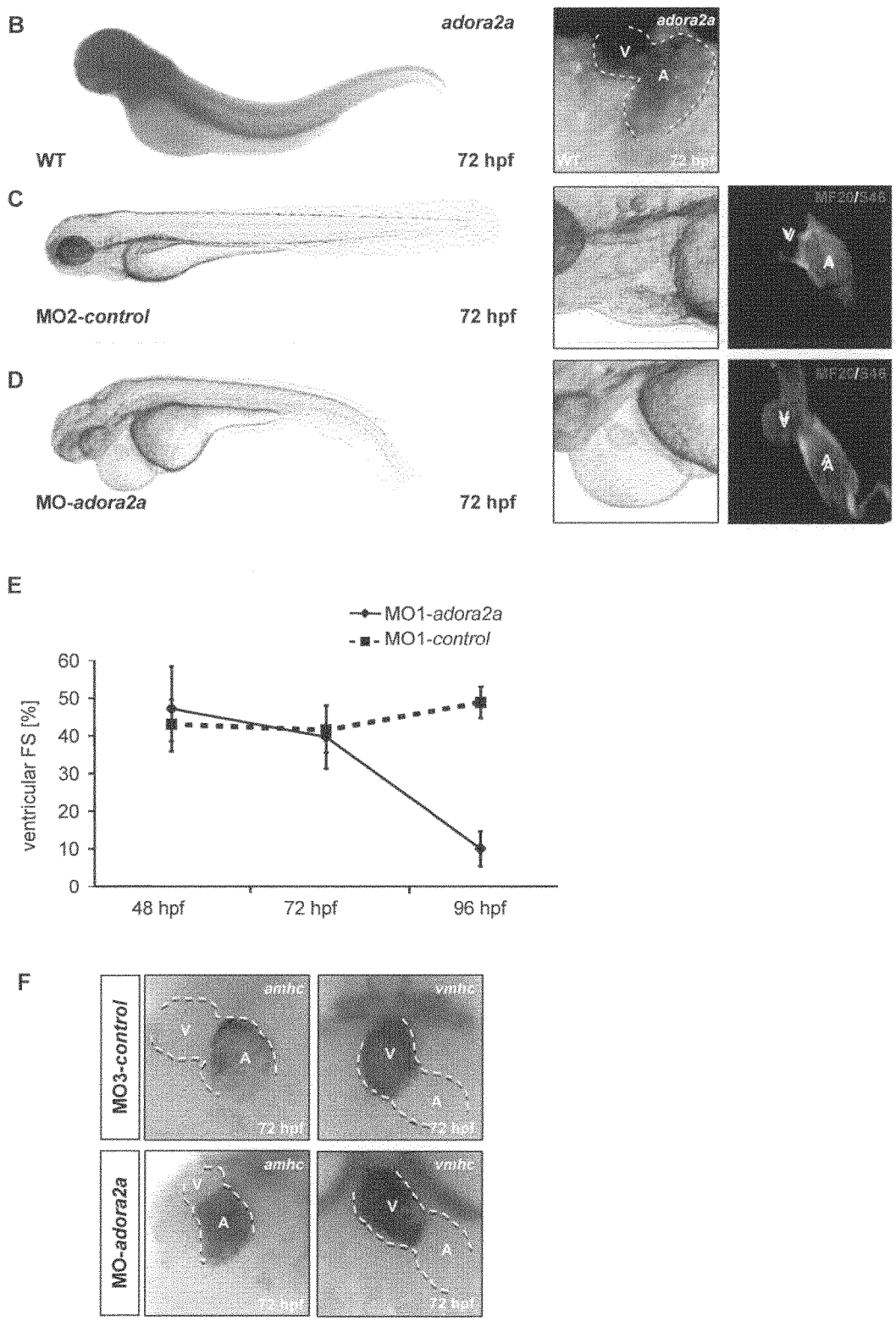

FIG. 9 Loss-of adora2a leads to heart failure in zebrafish.

A) Amino acid sequence alignments of human (h) (SEQ ID NO:98), mouse (m) (SEQ ID NO:99) and zebrafish (z) (SEQ ID NO:100) ADORA2A demonstrating its high cross-species homology. Black boxes indicate amino acid identity, gray boxes indicate amino acids with similar chemical properties. B) Adora2A is significantly expressed in the zebrafish heart. C, D) Lateral view of M02-control (B), and MO-adora2a (C) injected embryos at 72 hpf. After injection of MO-adora2a, 66% of morphant embryos develop progressive heart failure and deterioration in ventricular contractility measured by fractional shortening (E) at the indicated developmental stages. Error bars indicating standard deviation. F) Molecular chamber definition is not impaired in adora2a-morphants compared to the control-injected zebrafish as demonstrated by regular amhc and vmhc expression.

Figure 10:
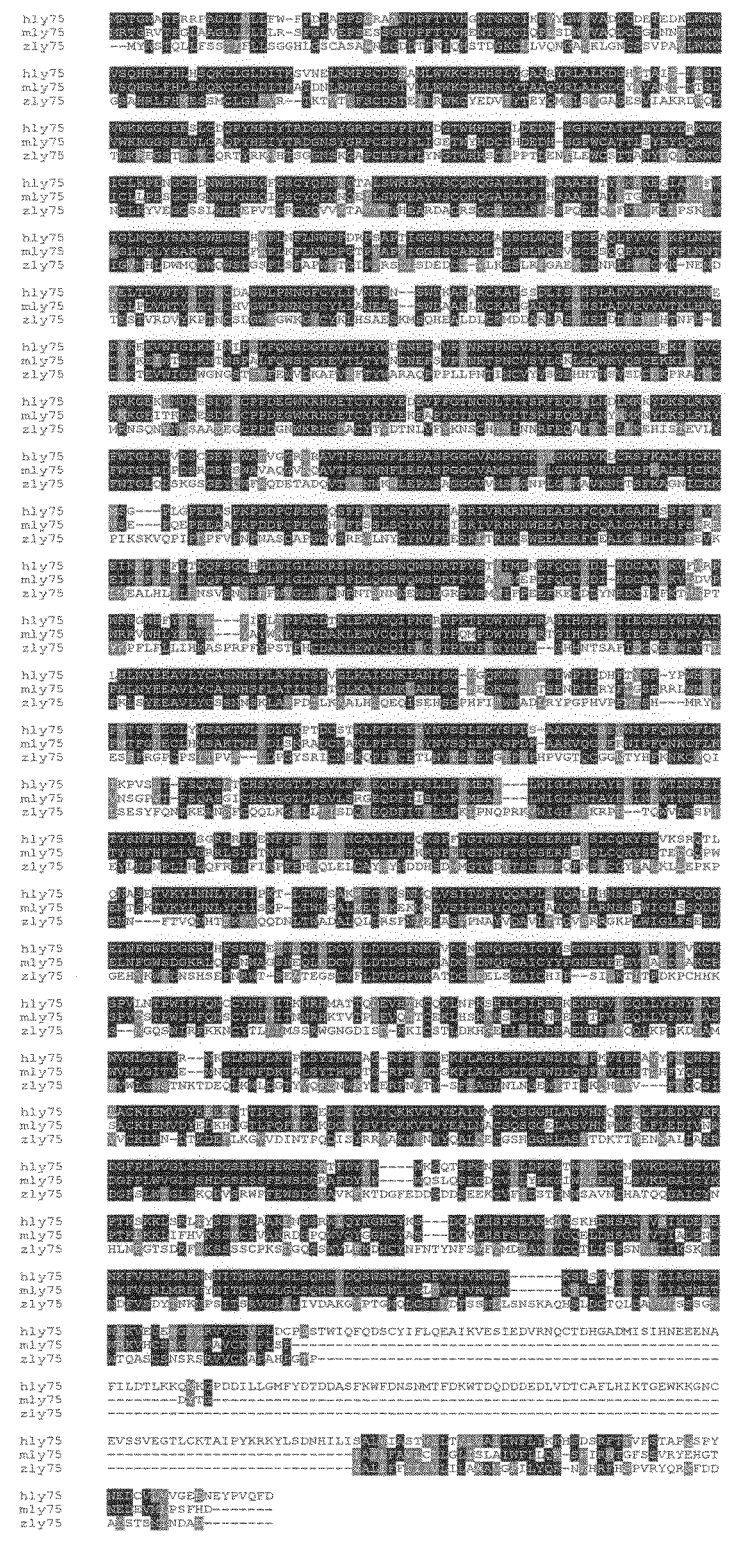

FIG. 10 Protein conservation of LY75.

Amino acid sequence alignments of human (h) (SEQ ID NO:101), mouse (m) (SEQ ID NO:102) and zebrafish (z) (SEQ ID NO:103) LY75 demonstrating its cross-species homology. Black boxes indicate amino acid identity, gray boxes indicate amino acids with similar chemical properties.

EXAMPLES

1. Materials and Methods
1.1 Patients and Controls

The study was conducted in accordance with the principles of the Declaration of Helsinki. All participants of the study have given written informed consent and the study was approved by the ethic committees. DCM was diagnosed according to the guidelines of the World Health Organization (WHO). Inclusion criteria for DCM cases were the presence of reduced left ventricular systolic function (left ventricular ejection fraction <45% assessed by echocardiography) in the absence of relevant coronary artery disease (CAD) as determined by coronary angiography. Patients with valvular or hypertensive heart disease, history of myocarditis, regular alcohol consumption or cardio-toxic chemotherapy were also excluded. The control biopsy specimens were obtained from patients who had received heart transplantation. All patients of the control cohort had successful cardiac transplantation more than 6 months ago with normal systolic and diastolic function and no evidence for relevant vasculopathy as judged by coronary angiography. Furthermore, all controls showed freedom from relevant acute or chronic organ rejection.

1.2 Processing of Left Ventricular Biopsies

Biopsy specimens were obtained from the apical part of the free left ventricular wall (LV) from DCM patients or cardiac transplant patients (controls) undergoing cardiac catheterization using a standardized protocol. Biopsies were washed with NaCl (0.9%) and immediately transferred and stored in liquid nitrogen until DNA or RNA was extracted. DNA was extracted using the DNeasy blood and tissue kit, total RNA using the RNeasy kit according to the manufacturer's protocol (Qiagen, Germany). RNA purity and concentration were determined using the Bioanalyzer 2100 (Agilent Technologies, Berkshire, UK) with a Eukaryote Total RNA Pico assay chip. Since a critical issue for the reliability of gene expression analysis is the quality of the RNA samples, a RNA integrity number (RIN)>6 was defined as minimum requirement for further analyses.

1.3 DNA Methylation Profiling and Fine-Mapping

For measuring methylation profiles, we used the Infinium HumanMethylation 27 BeadChip assay from Illumina with 1000 ng DNA per sample. The procedure followed the manufacturers standard workflow, starting with the bisulfite treatment of the sample DNA leading to a conversion of unmethylated cytosins to uracil, while 5-methylcytosines remain unchanged. After amplification and fragmentation of the bisulfite-converted DNA, they were hybridized to the Infinium BeadChips.

1.4 DNA Methylation Validation by MassARRAY

DNA methylation was validated by the MassARRAY technique as previously described (Ehrich et al., 2005). Briefly, 400-500 ng genomic DNA was chemically modified with sodium bisulfite using the EZ methylation kit (Zymo Research) according to the manufacturer's instructions. The bisulfite-treated DNA was PCR-amplified by primers designed to cover the Infinium probes that showed differential methylation at each locus. The amplicons were transcribed by T7 polymerase, followed by T specific-RNAase-A cleavage. The digested fragments were quantified by MALDI-TOF-based technique. The primer sequences are given in Table 1. DNA methylation standards (0%, 20%, 40%, 60%, 80%, and 100% methylated genomic DNA) were used to confirm the unbiased amplification of the amplicons. For LY75 and ADORA2A we additionally generated 14 and 12 clones, respectively, from 2 patients with DCM and 2 controls, each, and sequenced them before and after treatment with bisulfite. The methylation data was statistically analyzed by Students t-test, or ANOVA, followed by Dunnett's multiple comparison.

TABLE 1

Primer Sequences for mean CpG-island methylation of candidate genes.

| Genes | Forward primers | Reverse primers |
|---|---|---|
| ADORA2A | TTTTTTAGGTGGGTGTTGGTAGTT (SEQ ID NO. 19) | AATTCCCCTAATCCAATAAAATTCC (SEQ ID NO. 20) |
| ATP2C1 | ATTGGATAAAGGTATAGTTGTTAAAAGAAG (SEQ ID NO. 21) | AACAATCACAATCTCAACAAACAAC (SEQ ID NO. 22) |
| CCDC59 | TTTTTAGTGGAAGTAGAGTGGGAAG (SEQ ID NO. 23) | TTAAAACAACCTCCTTACACAATCC (SEQ ID NO. 24) |
| CLDN4 | GTTTATTTATAGGTTTTTTTAGATGGTTTG (SEQ ID NO. 25) | CATCAAAACTAACTTTATCTCCTAACTCA (SEQ ID NO. 26) |
| ERBB3 | GGAGATTTTTTAGTAGAGAATAGGTTTTTT (SEQ ID NO. 27) | TACTACCCAAAACCCTACTAATCCC (SEQ ID NO. 28) |
| FDX1 | TTTGTTTTATAGTGGGTAGAATTTATTT (SEQ ID NO. 29) | AACCTATAAAAACATTAACAAACAAAAC (SEQ ID NO. 30) |
| FLJ20701 | GATTTTAAATTTTAGTGAGGGGTGAA (SEQ ID NO. 31) | TCCAAAACAAAAAATAAACTCCAAA (SEQ ID NO. 32) |
| GFI1 | TTTATTTTAATGAGTAAAGGGTGTAGGT (SEQ ID NO. 33) | CCTAAAATCATACCCAAACACTAAAT (SEQ ID NO. 34) |
| GSTM5 | GGAGGGGGTTTATTGATTTTAGTTT (SEQ ID NO. 35) | TAACTTTCTCTACACCAAACCAACC (SEQ ID NO. 36) |
| HOXB13 | GGTAGTTTTTGGTTTTGGGTTTT (SEQ ID NO. 37) | ACTATCCCTAAATCTCATCTCTCCC (SEQ ID NO. 38) |
| ID4 | AATGGAGTGTTTTTTTATTGGTT (SEQ ID NO. 39) | AATATCCTAATCACTCCCTTC (SEQ ID NO. 40) |
| LY75 | GTATTTTGTTTAGGTTTTTGGGG (SEQ ID NO. 41) | AAAAATCATAAATCCCTTTCCAATC (SEQ ID NO. 42) |
| NAT1 | TTTTTTTAGGAAGTAAAAGGAATGTT (SEQ ID NO. 43) | TCAAACTACCCTAATCTCACTATCCC (SEQ ID NO. 44) |
| PPARGC1A | GATTTTTTAAAAGTTTTTGTTTGG (SEQ ID NO. 45) | ACAAATACCTTCAATTCACTCTCAA (SEQ ID NO. 46) |
| SLC9A6 | GTTTTTGATTGGGTAGGGGT (SEQ ID NO. 47) | AACTTACCATAAATCATAACCAAACC (SEQ ID NO. 48) |
| SULF2 | GAGTTTTGTGAAAGTAGATAAAAGAAAAT (SEQ ID NO. 49) | TAACACACAAACCAAAAAACATC (SEQ ID NO. 50) |
| TDG | TGGTTGGTAGTATTTAGATAGTGGTTG (SEQ ID NO. 51) | ATATACACAACACCCCAAAAACAA (SEQ ID NO. 52) |
| TFF1 | AGGTTGTTAGAGTTGGTTGTGGTT (SEQ ID NO. 53) | AACTTTCTAAATCTCAAATCCCTCAA (SEQ ID NO. 54) |
| TKT | GGGAAGGTTATTATTATTGTTGTTTT (SEQ ID NO. 55) | AAATCCCAAAATTCTACACCCA (SEQ ID NO. 56) |
| XRCC5 | GTTTTTTGTTAGGTTTGAAAGGGG (SEQ ID NO. 57) | AAAAAAAATCTAACTCCAAAACTCTAA (SEQ ID NO. 58) |

The respective target genomic sequences are shown in SEQ ID NOs. 59 to 78:

target genomic sequence of gene

| | |
|---|---|
| ADORA 2A | SEQ ID NO. 59; |
| ATP2C1 | SEQ ID NO. 60; |
| CCDC59 | SEQ ID NO. 61; |
| CLDN4 | SEQ ID NO. 62; |
| ERBB3 | SEQ ID NO. 63; |
| FDX1 | SEQ ID NO. 64; |
| FLJ20701 | SEQ ID NO. 65; |
| GFI1 | SEQ ID NO. 66; |

-continued

| | |
|---|---|
| GSTM5 | SEQ ID NO. 67; |
| HOXB13 | SEQ ID NO. 68; |
| ID4 | SEQ ID NO. 69; |
| LY75 | SEQ ID NO. 70; |
| NAT1 | SEQ ID NO. 71; |
| PPARGC1A | SEQ ID NO. 72; |
| SLC9A6 | SEQ ID NO. 73; |
| SULF2 | SEQ ID NO. 74; |
| TDG | SEQ ID NO. 75; |

-continued

| | |
|---|---|
| TFF1 | SEQ ID NO. 76; |
| TKT | SEQ ID NO. 77; |
| XRCC5 | SEQ ID NO. 78. |

1.5 Promoter Luciferase Assay

To assess the causative link of CGI methylation within the promoter region of LY75 with reduced mRNA expression observed in myocardial tissue, we performed a promoter luciferase assay essentially as described before (Smith et al., 2006). Therefore, we cloned a 1.6 kb large core fragment (Table 2) of the LY75 promoter region including the analyzed CGI into SpeI/BamHI sites of the CpG-free luciferase vector pCpGL-basic. As negative control for the methylation effect we utilized the CpG-free control reporter vector pCpGL-CMV/EF1 (Klug and Rehli, 2006). Next, we treated both vectors with the methylase SssI (New England Bio-Labs) or leaved them untreated, respectively. The methylation was performed at 10 mM Tris, pH7.9, 50 mM NaCl, 10 mM $MgCl_2$, 1 mM DTT and 160 µM SAM at 37° C. for 1 hour (Blesa et al., 2008). Transfection of human HEK293A cells with equal amounts of the SssI-treated or untreated pCpG-LY75 or pCpGL-CMV/EF1 vectors was carried out using Lipofectamin (Invitrogen). Additionally, we co-transfected these cells with the pGL4.74 [hRluc/TK] *Renilla* control vector as a reference (Promega). After 48 hours, cells were lysed and luciferase and *Renilla* activity measured according to manufactures protocol (Dual-Luciferase Reporter Assay System, Promega). Results are expressed as relative luciferase activity (background subtracted and normalized to *Renilla* reference; three technical replicates) of the methylated versus the unmethylated constructs.

TABLE 2

Primer sequences for promoter luciferase assay.

| Gene | Forward primer | Reverse primer |
|---|---|---|
| LY75 | TGGCACTACCCTGAACATCA (SEQ ID NO. 79) | CATGAAATTTCTGGTTCTGCAT (SEQ ID NO. 80) |

The respective target genomic sequence is shown in SEQ ID NO. 81.

1.6 Promoter Region Prediction and Transcription Factor Binding Site Analysis

We applied the Promoter 2.0 Prediction Software that predicts transcription start-sites (TSS) of vertebrate Pol II promoters in genomic DNA to estimate the distance of the CGIs from the potential transcriptional start-sites (Knudsen 1999). For the detection of transcription factor binding sites, the ENCODE transcription factor ChIP-seq data was used. For each region (size of the CGI and 1500 bp up- and downstream), we selected in the maximum the three factors up- and three factors downstream with strongest observed binding.

1.7 Hierarchical Clustering

To generate a graphical representation of the most significantly dys-methylated cardiac genes in the screening stage and to detect patterns among the respective genes, hierarchical clustering was applied. Prior to the clustering, the patients were ranked for each gene according to the degree of methylation, i.e., the patient with the lowest degree of methylation for a certain gene received a rank of 1, while the patient with the highest degree of methylation received a rank of 17, since 17 samples have met filter criteria for the screening stage. Then, for all samples and all genes the pair-wise Euclidian distances were computed and a bottom-up clustering on these distances was carried out. All computations were carried out using the statistical programming language R.

1.8 Gene Network Analysis

To test whether genes with differential methylation patterns belong to a certain biological category we carried out an unweighted Gene Set Enrichment Analysis (GSEA). In detail, we first sorted all genes according to the absolute value of the median distances between DCM patients and controls, generated a sorted list of genes where the most differentially methylated genes were on top while genes without differential methylation were located at the bottom of the list. If one gene was represented by multiple features on the biochip (different methylation sites) the median position of all replicates in the sorted list was computed. This sorted list was then used as input for GeneTrail (Backer et al. 2007). For each category, a significance value is computed by a dynamic programming approach (Keller et al. 2007) and all significance values of a certain category have been adjusted for multiple testing using Benjamini-Hochberg adjustment (Benjamini and Hochberg, 1995). The advantage of the applied cutoff-free biostatistical approach is that genes with p-values of 0.049 and 0.051 are considered to be almost equally important in our approach while genes with larger values in the middle and at the end of the list are considered to be not of relevance. In contrast, classical over-representation analyses relying on cutoffs (usually 0.05) would consider genes with p-value of 0.049 of relevance while genes with p-values of 0.051 would be considered to be non-relevant, having the same impact as genes with large p-values.

1.9 Transcriptomic Analyzes

Quantitative real-time PCR (q-PCR) was performed in order to measure expression of selected genes. Primers were designed using NCBI Primer-Blast and synthesized by Eurofins MWG Operon (Ebersberg, Germany). 60 ng of total RNA extracted from biopsies of independent DCM patients (moderate: n=7; severe: n=5) and controls (n=7) was reverse transcribed using SuperScript III first strand cDNA synthesis kit (Invitrogen). q-PCR was carried out according to standard protocols with the SYBR-Green method (Thermo Scientific) using an ABI 7000 system (ABI). Specificity of each primer-pair was monitored by dissociation curve analysis. Threshold cycle (CT) values were assessed in the exponential phase of amplification and the data were analyzed using the delta-CT method. The mean value of the reference genes GAPDH, RPL13 and â-actin was used as a reference.

To identify the predominant cardiac isoform of ADORA2A, we performed PCR with the following primer-pair for both isoforms (ENST00000337539 and ENST00000541988):

[SEQ ID NO. 82]
5'-CTGTGACATGGAGCAGGAGC-3'
and

[SEQ ID NO. 83]
5'-GCTGTCGTTTGCCATCGGCCT-3'.

To evaluate the expression levels of ly75 and adora2a in the zebrafish heart and whole organism, we performed q-PCR with the following primer-pair for ly75:

```
5'-CATGGCCAGTTTCGATCCAT-3'          [SEQ ID NO. 84]
and
5'-CACCTGGGACTACACCTCCT-3'          [SEQ ID NO. 85]
``` and adora2a:

```
5'-TGCTGACCCAGAGCTCCATA-3'          [SEQ ID NO. 86]
and
5'-AGAGGCATCATCGCGATCTG-3'.         [SEQ ID NO. 87]
```

Results are shown as relative expression values (normalization against the house-keeping gene elf1a).

To analyze the expression of ly75 and adora2a in different cell types, we cultured neonatal rat cardiomyocytes and cardiofibroblasts for 5 days and proceeded as described above. q-PCR was performed using the primer pairs

```
18s RNA
5'-GGACATCTAAGGGCATCAC-3'           [SEQ ID NO. 88]
and
5'-CCTCCGACTTTCGTTCTTGA-3';         [SEQ ID NO. 89]

LY75
5'-CACGGTCTGATGAGCTGTGT-3'          [SEQ ID NO. 90]
and
5'-ACGAACTGCAACCTGACCAT-3';         [SEQ ID NO. 91]

ADORA2A
5'-CTGGTCCTCACGCAGAGTTC-3'          [SEQ ID NO. 92]
and
5'-GCGAAGGGCATCATTGCAAT-3'.         [SEQ ID NO. 93]
```

The methylation data was statistically analyzed by Students t-test.

1.10 Morpholino-Mediated Gene Knock-Down in Zebrafish

The zebrafish experiments were performed under institutional approvals that conform to the Guide for the Care and Use of Laboratory Animals published by The US National Institute of Health (NIH Publication No. 85-23, revised 1996). Care and breeding of zebrafish (*Danio rerio*) were as described (Meder et al. 2011).

The following Morpholino-modified antisense oligonucleotides (GeneTools, USA) were designed:

The ly75 (ENSDARG00000053113) Morpholino targets the splice-donor site of exon 3:

```
MO-ly75:
5'-GTGATGAAACGCACACCTCTCCTGA-3';    [SEQ ID NO. 94]

scrambled control MO3-control:
5'-GTCATGAAAGGCACACGTCTGCTCA-3'),   [SEQ ID NO. 95]
``` while adora2a (ENSDARG00000033706) was targeted at its start-site:

```
MO-adora2a:
5'-CATTGTTCAGCATGGTGAGGTCGCT-3';    [SEQ ID NO. 96]

scrambled control MO2-control:
5'-CATTCTTCACCATCGTGACGTGGCT-3'.    [SEQ ID NO. 97]
```

Morpholinos or control oligonucleotides (MO-control) were injected into 1-cell stage embryos as described before (Meder et al. 2009). To confirm the efficiency of splice-site Morpholinos, we analyzed their target region by cDNA splice-site analysis (Meder et al. 2011).

1.11 Functional Assessment and Statistical Analysis of Cardiac Function

Still images and video films were recorded and digitized with a Zeiss microscope/MCU II. The functional assessment of cardiac contractility was carried out as described before (Meder et al. 2009). Atrial and ventricular diameters were measured to calculate fractional shortening with the help of the zebraFS software (http://www.mederlab.com). Results are expressed as mean±standard deviation. MF20/S46 stainings and mRNA antisense in situ hybridization was performed as described previously (Meder et al. 2009).

2. Results 2.1 DNA Methylation is Altered in Patients with DCM

We performed here a two-staged, funnel-like DNA methylation mapping in non-ischemic, idiopathic DCM patients and controls (Table 3).

TABLE 3

Study sample characteristics of the screening and replication cohorts.

| Cohort | N | Female (%) | Age (years) | LV-EF (%) |
|---|---|---|---|---|
| Screening | | | | |
| DCM cases | 9 | 33 | 57 ± 5.4 | 27 ± 7.5 |
| Controls | 8 | 38 | 42 ± 14 | 60 ± 4 |
| Replication | | | | |
| DCM Cases | 30 | 37 | 58 ± 14 | 25.6 ± 8.4 |
| Controls | 28 | 46 | 57 ± 12 | 61.5 ± 5.3 |

Female = female donor status of transplanted heart;
LV-EF = left ventricular ejection fraction.

Figure 1:
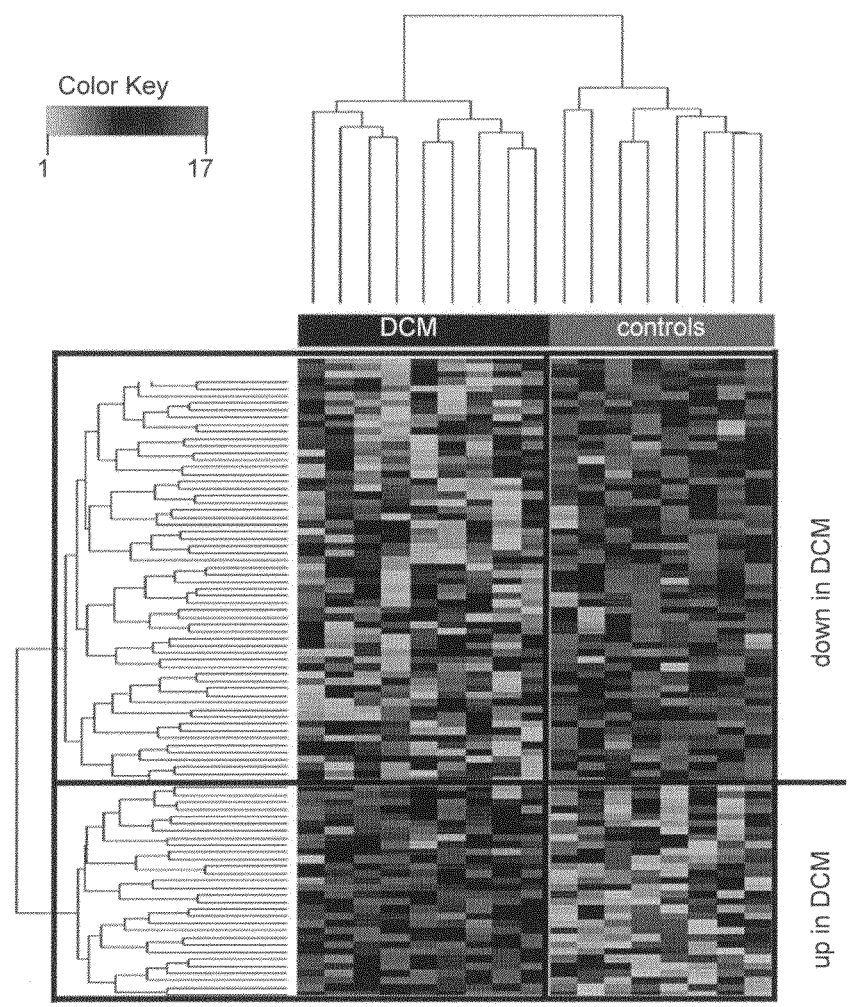
FIG. 1 Detection of DNA methylation patterns.

In the screening stage, we assessed genome-wide DNA methylation levels of CpG islands (CGIs) using the Infinium HumanMethylation 27 platform. To do so, we first extracted 1000 ng of genomic DNA from LV biopsies from 10 DCM patients and 10 controls. After methylation profiling, 17 datasets passed the stringent quality filter criteria, exemplarily shown by reaching highly similar bead color signal intensities (data not shown). FIG. 1A shows a correlation-plot of the 27,578 individual methylation-sites for all further analyzed patients and controls. While the degree of methylation for most CpG sites is highly correlated between the two groups, we detect several CGIs that are hypo- (green dots) or hyper-methylated (red dots) in DCM compared to the controls (unadjusted p-value <0.05).

We used the comprehensive screening datasets in a Gene Set Enrichment Analysis (GSEA) and identified within the top three (ranked by p-values) enriched disease categories provided by the "National Institute of Aging" (NIA) the disease pathways "Cardiovascular Disease", "Metabolic Disease", and "Pathological Conditions", all reasonably associated with DCM and with considerable overlaps between each other (FIG. 1B). To detect patterns of genes with differential methylation in the screening cohorts, we carried out a clustering approach on genes with known abundant expression in the human heart (http://c-it.mpi-bn.mpg.de). From the annotated 2,018 individual genes, 1,858 (92.1%) were covered by the applied Infinium assay. Since the degrees of methylation for the genes were not normally distributed, we used two-tailed Wilcoxon rank-sum test to compute a significance value for each gene, which resulted in a total of 90 genes surpassing statistical significance (p-value <0.05). While about one third showed increased methylation in DCM patients, approximately two thirds were significantly less methylated. FIG. 1C gives a graphical representation of differential methylation patterns by using hierarchical clustering on the Euclidian distance. The heat map shows the patterns of higher- and lower methylated genes in DCM patients and controls.

For the replication stage in an independent cohort, methylation patterns of single genes were used to define candidates for a mass-spectrometry-based fine-mapping. FIGS. 2A and B show the five most hyper- and hypomethylated genes, while C details the 20 most significantly dys-methylated genes of the screening stage. The final selection was based on either unadjusted p-values or absolute methylation difference, CGI localization, capability to design specific assay probes, and known expression in the heart.

2.2 Validation of Aberrant DNA Methylation in DCM

As denoted above, we carried out an independent replication and fine-mapping of the selected genes in a larger cohort of 30 idiopathic DCM patients and 28 controls. The selected candidates were fine-mapped by using MassARRAY (Ehrich et al. 2005).

For each gene, several CpGs were retrieved and their methylation status quantified. From 20 candidate genes, twelve showed the same direction of altered methylation between the screening and the replication stage and four of them reached statistical significance, namely LY75 (p=0.000), ERBB3 (p=0.013), HOXB13 (p=0.001), and ADORA2A (p=0.011). FIG. 3 presents the mean methylation changes of the replicated genes. Additionally, methylation of individual CpGs is displayed for LY75 and ERBB3 (FIG. 3A, B), HOXB13 (FIG. 3C) and ADORA2A (FIG. 3D). Interestingly, ADORA2A showed significantly altered methylation throughout all tested CpGs, while ERBB3 or LY75 showed methylation alterations in a subset of the CpG nucleotides, possibly resulting in different functional consequences. FIG. 4 gives the mean methylation of the rest of the investigated CGIs. Since epigenetic marks may be also dependent on the gender, we additionally matched the gender ratio of cases and controls of the replication cohort to the ratio of the screening cohort, leading to significance of the same CGIs shown above. This is also true when matching females and males 1:1.

In addition to MassARRAY, we also applied bisulfite sequencing for LY75 and ADORA2A to fine-map and again technically replicate our results. To do so, we generated 14 LY75 and 12 ADORA2A clones from two DCM patients and two controls each, and sequenced them before and after treatment with bisulfite (FIG. 3A and FIG. 3D; black circles=methylated CpG, white circles=unmethylated CpG). Bisulfite sequencing confirmed the corresponding MassARRAY data and, hence, demonstrated reliability of the latter technique.

Next, to rule out a potential effect of the immunosuppressive medication received by the control subjects (Table 4) on the methylation of the here investigated genes, we analyzed the methylation patterns of genomic DNA of 11 subjects drawn pre- and post-heart transplantation (HTX) (mean timespan after HTX=37 months under medication). As shown in FIG. 5 we found highly comparable methylation levels (p=n.s.) of LY75, ADORA2A, ERBB3, and HOXB13 CGIs in pre- and post-HTX, indicating that the observed methylation differences in DCM is not due to methylation changes in the controls receiving immunosuppressive medication.

TABLE 4

Immunosuppressive medication of control individuals.

| Medication | N | % |
| --- | --- | --- |
| Tacrolimus | 19 | 54 |
| Mycophenolat- | 23 | 66 |
| Ciclosporin | 8 | 23 |
| Prednisolon | 11 | 31 |
| Everolimus | 14 | 40 |

All control individuals received one or more immunosuppressives.

2.3 Differential Gene Expression and Functional Evaluation In Vivo Points Towards a Functional Role of Altered DNA Methylation in DCM DNA methylation is often correlated with changes in the accessibility of DNA to transcriptional activators, enhancers, or repressors. Hence, we first studied the impact of DNA methylation at LY75, ERBB3, HOXB13, and ADORA2A loci on their gene expression by quantitative PCR (q-PCR) in controls, mild DCM (NYHA class II) and moderate to severe DCM (NYHA class III-IV).

For ADORA2A, we found a positive relationship of gene expression with methylation (relative expression=0.33; p=0.002), while ERBB3 did not show significant alterations in cardiac expression levels (FIG. 6B, C, D). HOXB13 transcripts could not be PCR amplified in LV biopsies from both, patients and controls. In case of LY75, the hypermethylated CpG island is relatively close to the transcriptional start-site (distance 1,395 bp), whereas the distance between the CGIs in ERBB3 (7,518 bp) and ADORA2A (14,329 bp) is markedly larger (FIG. 3). Since we observed also a strong reduction in LY75 expression in myocardial tissue (relative expression=0.04; p=0.001) in patients with DCM (FIG. 6A, D), we asked if increased promoter methylation is directly responsible for decreased transcriptional activity. Hence, we performed a luciferase promoter assay with methylated and unmethylated LY75 promoters. As a negative control served the CpG-free control reporter vector pCpGL-CMV/EF1. As shown in FIG. 6E, we found a strong reduction in promoter activity after in vitro methylation, supporting the functional relationship between LY75 hypermethylation and reduced expression in human DCM.

Since we found a rather unusual positive relationship of ADORA2A gene expression and methylation, we first sought to identify the predominant isoform of ADORA2A in the human myocardium. By PCR, we found that the longer ADORA2A transcripts ENST00000337539 and ENST00000541988 are highly expressed in the heart. However isoform ENST00000417596, which is highly expressed in peripheral blood, is not significantly expressed in the heart. We then investigated potential repressor regions in the close vicinity of the tested CGIs. For the detection of transcription factor binding sites, the ENCODE transcription factor ChIP-seq data was used. We found for the aberrantly methylated CGI-1 two potential repressor sites (CTCF and NFKB), for aberrantly methylated CGI-2 one repressor site (CTCF) and for the unaltered CGI-3 one repressor site (Max). Interestingly, both hypomethylated CGIs (1 and 2) carry CTCF binding sites, which were recently identified as epigenetic key regulators in various other diseases.

Since LY75 and ADORA2A were not previously known to be involved in DCM or heart failure pathogenesis and both showed significant downregulation in the myocardium of DCM patients, we investigated their functional roles by gene knockdown in zebrafish embryos (Dahme et al., 2009). We identified orthologous sequences for human LY75 and ADORA2A by BLAST searches against the zebrafish Genbank database. Protein sequence identity between the zebrafish and human version was 61% for adora2a (FIG. 9A) and 37% for ly75 (FIG. 10). Similar to the human situation, we found adora2a and ly75 to be highly expressed in the zebrafish heart using q-PCR and RNA antisense in-situ hybridization (FIGS. 7, 8 and 9). Additionally, as shown in cultured neonatal rat cells, both genes are higher expressed in cardiomyocytes than in cardiofibroblasts (FIG. 7B, C). Hence, to recapitulate the downregulation of both genes as observed in the human heart, we inactivated them in zebrafish embryos by injection of Morpholino-modified antisense oligonucleotides directed against the splice donor-site of ly75 or the translational start-site of adora2a. While control-injected zebrafish (standard control Morpholino as well as scrambled control Morpholinos) embryos did not show any obvious phenotype, splice-site Morpholino-mediated knockdown of ly75 resulted in partial skipping of exon 8 (FIG. 8D) and consecutive frameshift that predictably leads to a premature stop of protein translation. As a result, ly75-morphants developed "late-onset" heart failure with dilation of the atrium (FIG. 8C) and reduced ventricular contractility beginning at the 96 hours developmental stage (FS=46±5% at 48 hpf and 29±4% at 96 hpf) (FIG. 8E). Additionally, ly75-morphants showed a pronounced detachment and edema of the skin especially noticeable in the eye and head region (FIG. 8C). MO-adora2a injected embryos also developed severe heart failure with progressively decreasing ventricular contractility as measured by fractional shortening (FIG. 9E). In detail, the ventricular contractility of adora2a-morphants decreased from 47±11% at 48 hpf to 39±8% at 72 hpf. By 96 hpf, both heart chambers became almost silent. Occasionally, we also observed atrial fibrillation in adora2a-morphants and embryos developed excessive pericardial effusion and precardial blood congestion as consequence of the reduced cardiac function. For both, ly75- and adora2a-morphants, we saw no alterations in the molecular chamber specification and expression of atrial and ventricular myosin heavy chain genes (FIGS. 8 and 9).

For investigating the functional role of ERBB3, we also used the zebrafish as animal model. We find homology of 56% between human and zebrafish orthologues sequence of ERBB3. Knock-down of erbb3b results in a similar, but earlier phenotype as adora2a. Already by 72 hpf, 86% of injected erbb3b-morphants suffer from significantly reduced cardiac contractility, reduced blood flow through the atrium and ventricle, and pericardial effusion (data not shown). FS at 96 hpf is reduced to 21±4% and blood aggregates at the cardiac inflow tract (data not shown). Additionally, erbb3b-morphants show regurgitation of blood into the ventricle (data not shown), suggesting impaired cardiac valve development. cDNA splice-site analysis revealed a completely insertion of intron 2 as well a partial exclusion exon 2 producing an aberrant, frameshifted transcripts with premature termination codons.

The features disclosed in the foregoing description, in the claims and/or in the accompanying drawings may, both separately and in any combination thereof, be material for realizing the invention in diverse forms thereof

REFERENCES

Backes C, Keller A, Kuentzer J, Kneissl B, Comtesse N, Elnakady Y A, Muller R, Meese E, Lenhof H P. GeneTrail—advanced gene set enrichment analysis. *Nucleic Acids Res* 2007; 35(Web Server issue):W186-92.

Backs J, Song K, Bezprozvannaya S, Chang S, Olson E N. CaM kinase II selectively signals to histone deacetylase 4 during cardiomyocyte hypertrophy. *J Clin Invest* 2006; 116(7):1853-64.

Backs J, Backs T, Bezprozvannaya S, McKinsey T A, Olson E N. Histone deacetylase 5 acquires calcium/calmodulin-dependent kinase II responsiveness by oligomerization with histone deacetylase 4. *Mol Cell Biol* 2008; 28(10): 3437-45.

Bell, A. C., A. G. West, and G. Felsenfeld, *The protein CTCF is required for the enhancer blocking activity of vertebrate insulators.* Cell, 1999. 98(3): p. 387-96.

Bell, A. C. and G. Felsenfeld, *Methylation of a CTCF-dependent boundary controls imprinted expression of the Igf2 gene.* Nature, 2000. 405(6785): p. 482-5.

Benjamini Y, Hochberg Y. Controlling the false discovery rate: A practical and powerful approach to multiple testing. *J R Statist Soc B* 1995; 57:289-300.

Bielecka-Dabrowa et al., New methods in laboratory diagnostics of dilated cardiomyopathy. *Cardiol J.* 2008; 15(4): 388-95

Blesa, J. R., A. A. Hegde, and J. Hernandez-Yago, *In vitro methylation of nuclear respiratory factor-2 binding sites suppresses the promoter activity of the human TOMM70 gene.* Gene, 2008. 427(1-2): p. 58-64.

Coppede F. Epigenetic biomarkers of colorectal cancer: focus on DNA methylation. *Cancer Lett* 2011.

Dahme, T., H. A. Katus, and W. Rottbauer, *Fishing for the genetic basis of cardiovascular disease.* Dis Model Mech, 2009. 2(1-2): p. 18-22.

Ehrich M, Nelson M R, Stanssens P, Zabeau M, Liloglou T, Xinarianos G, Cantor C R, Field J K, van den Boom D. Quantitative high-throughput analysis of DNA methylation patterns by base-specific cleavage and mass spectrometry. *Proc Natl Acad Sci USA* 2005; 102(44):15785-90.

Erickson S L, O'Shea K S, Ghaboosi N, Loverro L, Frantz G, Bauer M, Lu L H, Moore M W. ErbB3 is required for normal cerebellar and cardiac development: a comparison with ErB2- and heregulin-deficient mice. *Development.* 1997 December; 124(24):4999-5011.

Feinberg A P, Tycko B. The history of cancer epigenetics. *Nat Rev Cancer* 2004; 4(2):143-53.

Friedrichs F, Zugck C, Rauch G J, Ivandic B, Weichenhan D, Muller-Bardorff M, Meder B, El Mokhtari N E, Regitz-Zagrosek V, Hetzer R, Schafer A, Schreiber S, Chen J, Neuhaus I, Ji R, Siemers N O, Frey N, Rottbauer W, Katus H A, Stoll M. HBEGF, SRA1, and IK: Three cosegregating genes as determinants of cardiomyopathy. *Genome Res* 2009; 19(3):395-403.

Gaszner, M. and G. Felsenfeld, *Insulators: exploiting transcriptional and epigenetic mechanisms.* Nat Rev Genet, 2006. 7(9): p. 703-13.

Giridhar P V, Funk H M, Gallo C A, Porollo A, Mercer C A, Plas D R, Drew A F. Interleukin-6 receptor enhances early colonization of the murine omentum by upregulation of a mannose family receptor, LY75, in ovarian tumor cells. *Clin Exp Metastasis* 2011; 28(8):887-97.

Grzeskowiak, R., et al., *Expression profiling of human idiopathic dilated cardiomyopathy.* Cardiovasc Res, 2003. 59(2): p. 400-11.

Hamad E A, Li X, Song J, Zhang X Q, Myers V, Funakoshi H, Zhang J, Wang J, Li J, Swope D, Madonick A, Farber J, Radice G L, Cheung J Y, Chan T O, Feldman A M. Effects of cardiac-restricted overexpression of the A(2A)

adenosine receptor on adriamycin-induced cardiotoxicity. *Am J Physiol Heart Circ Physiol* 2010; 298(6):H1738-47.

Herceg Z, Vaissiere T. Epigenetic mechanisms and cancer: an interface between the environment and the genome. *Epigenetics* 2011; 6(7):804-19.

Jirtle R L, Skinner M K. Environmental epigenomics and disease susceptibility. *Nat Rev Genet* 2007; 8(4):253-62.

Jones P A, Baylin S B. The fundamental role of epigenetic events in cancer. *Nat Rev Genet* 2002; 3(6):415-28.

Keller A, Backes C, Lenhof H P. Computation of significance scores of unweighted Gene Set Enrichment Analyses. *BMC Bioinformatics* 2007; 8:290.

Klug, M. and M. Rehli, *Functional analysis of promoter CpG methylation using a CpG-free luciferase reporter vector*. Epigenetics, 2006. 1(3): p. 127-30.

Knudsen, S., *Promoter2.0: for the recognition of PolII promoter sequences*. Bioinformatics, 1999. 15(5): p. 356-61.

Litzow M R. Novel therapeutic approaches for acute lymphoblastic leukemia. *Hematol Oncol Clin North Am* 2011; 25(6):1303-17.

Meder B, Laufer C, Hassel D, Just S, Marquart S, Vogel B, Hess A, Fishman M C, Katus H A, Rottbauer W. A single serine in the carboxyl terminus of cardiac essential myosin light chain-1 controls cardiomyocyte contractility in vivo. *Circ Res* 2009; 104(5):650-9.

Meder B, Huttner I G, Sedaghat-Hamedani F, Just S, Dahme T, Frese K S, Vogel B, Kohler D, Kloos W, Rudloff J, Marquart S, Katus H A, Rottbauer W. PINCH proteins regulate cardiac contractility by modulating integrin-linked kinase-protein kinase B signaling. *Mol Cell Biol* 2011; 31(10:3424-35.

Meurs K M, Kuan M. Differential methylation of CpG sites in two isoforms of myosin binding protein C, an important hypertrophic cardiomyopathy gene. *Environ Mol Mutagen* 2011; 52(2):161-4.

Montgomery R L, Davis C A, Potthoff M J, Haberland M, Fielitz J, Qi X, Hill J A, Richardson J A, Olson E N. Histone deacetylases 1 and 2 redundantly regulate cardiac morphogenesis, growth, and contractility. *Genes Dev* 2007; 21(14):1790-802.

Movassagh M, Choy M K, Knowles D A, Cordeddu L, Haider S, Down T, Siggens L, Vujic A, Simeoni I, Penkett C, Goddard M, Lio P, Bennett M R, Foo R S. Distinct epigenomic features in end-stage failing human hearts. *Circulation* 2011; 124(22):2411-22.

Smith, L. T., et al., *Epigenetic regulation of the tumor suppressor gene TCF21 on 6q23-q24 in lung and head and neck cancer*. Proc Natl Acad Sci USA, 2006. 103(4): p. 982-7.

Sommerschild H T, Kirkeboen K A. Adenosine and cardioprotection during ischaemia and reperfusion—an overview. *Acta Anaesthesiol Scand* 2000; 44(9):1038-55.

Takai D, Jones P A. Comprehensive analysis of CpG islands in human chromosomes 21 and 22. *Proc Natl Acad Sci USA* 2002; 99(6):3740-5.

Talens, R. P., et al., *Variation, patterns, and temporal stability of DNA methylation: considerations for epigenetic epidemiology*. Faseb J, 2010. 24(9): p. 3135-44.

Timonen P, Magga J, Risteli J, Punnonen K, Vanninen E, Turpeinen A, Tuomainen P, Kuusisto J, Vuolteenaho O, Peuhkurinen K. Cytokines, interstitial collagen and ventricular remodelling in dilated cardiomyopathy. *Int J Cardiol* 2008; 124(3):293-300.

Urmaliya V B, Church J E, Coupar I M, Rose'Meyer R B, Pouton C W, White P J. Cardioprotection induced by adenosine A1 receptor agonists in a cardiac cell ischemia model involves cooperative activation of adenosine A2A and A2B receptors by endogenous adenosine. *J Cardiovasc Pharmacol* 2009; 53(5):424-33.

Villard E, Perret C, Gary F, Proust C, Dilanian G, Hengstenberg C, Ruppert V, Arbustini E, Wichter T, Germain M, Dubourg O, Tavazzi L, Aumont M C, Degroote P, Fauchier L, Trochu J N, Gibelin P, Aupetit J F, Stark K, Erdmann J, Hetzer R, Roberts A M, Barton P J, Regitz-Zagrosek V, Aslam U, Duboscq-Bidot L, Meyborg M, Maisch B, Madeira H, Waldenstrom A, Galve E, Cleland J G, Dorent R, Roizes G, Zeller T, Blankenberg S, Goodall A H, Cook S, Tregouet D A, Tiret L, Isnard R, Komajda M, Charron P, Cambien F. A genome-wide association study identifies two loci associated with heart failure due to dilated cardiomyopathy. *Eur Heart J* 2011.

Zhang X, Yazaki J, Sundaresan A, Cokus S, Chan S W, Chen H, Henderson I R, Shinn P, Pellegrini M, Jacobsen S E, Ecker J R. Genome-wide high-resolution mapping and functional analysis of DNA methylation in *arabidopsis*. *Cell* 2006; 126(6):1189-201.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09938580B2). An electronic copy of the "Sequence Listing" will also be available from the USPTO upon request and payment of the fee set forth in 37 CFR 1.19(b)(3).

The invention claimed is:

1. A method for analyzing LY75 gene methylation in a sample from a patient, the method comprising:

determining a DNA methylation level of a target genomic sequence in genomic DNA obtained from a patient sample and a control sample from a subject not having DCM or having a normal heart function, the patient sample and the control sample comprising heart cells or heart tissue, wherein said determining the DNA methylation level of the target genomic sequence comprises the steps of:

i) isolating the genomic DNA from the patient sample and the control sample, ii) bisulfite treating the genomic DNA from the patient sample and the control sample;

iii) PCR amplifying the target genomic sequence from the bisulfite treated genomic DNA from the patient sample and the control sample using a primer pair having the sequence of SEQ ID NOs. 41 and 42;

iv) determining the DNA methylation level of the target genomics sequences in the patient sample and the control sample; and v) comparing the level of DNA methylation in the target genomic sequence in the patient sample to the level of DNA methylation in the target genomic sequence of the control sample.

2. The method according to claim 1, wherein the DNA methylation of the patient sample has a different degree of CpG methylation compared to the DNA methylation of the control sample.

3. The method according to claim 1, wherein the DNA methylation level of the target genomic sequence in the patient sample is determined before and after a therapy is provided to the patient and the DNA methylation level of the target genomic sequence in the patient sample before and after the therapy is used for determining the effects of the therapy provided to the patient.

4. The method according to claim 1, wherein the patient sample is a sample of left ventricular tissue.

5. The method according to claim 1, further comprising providing a prognosis of DCM or heart failure comprises risk stratification and/or disease classification.

6. The method according to claim 1, the method further comprising determining the methylation level of at least one of SEQ ID NOs. 1-2 and 4-18 in a patient sample and the control sample.

7. The method according to claim 6, wherein the patient sample is a sample of left ventricular tissue.

8. The method according to claim 3, wherein the therapy monitoring comprises treatment monitoring, treatment decision making, and the prediction of therapy effects or method.

9. A method for amplifying a target genomic sequence in genomic DNA obtained from a patient sample, and, optionally a control samples, the patient sample and the control sample compromising heart cells or heart tissue, wherein said amplifying the target genomic sequence comprises i) isolating genomic DNA from the patient sample and, optionally, the control sample ii) bisulfite treating the isolated genomic DNA, and iii) PCR amplifying the bisulfite treated genomic DNA with a primer pair having the sequences of SEQ ID NOs. 41 and 42.

10. The method of claim 1, wherein the step v) comprises comparing the mean CpG methylation level of the target genomic sequence in the patient sample with the mean CpG methylation level of the target genomic sequence in the control sample.

11. A method of amplifying a target genomic sequence in genomic DNA of a human cell, the method comprising the steps of:

i) isolating the genomic DNA from the human cell, ii) bisulfite treating the isolated genomic DNA, and iii) PCR amplifying the bisulfite treated genomic DNA with a primer pair having the sequences of SEQ ID NOs. 41 and 42.

12. The method according to claim 1, the method further comprising providing an indication of the presence or absence of dilated cardiomyopathy (DCM) or heart failure in the patient.

* * * * *

UNITED STATES PATENT AND TRADEMARK OFFICE
CERTIFICATE OF CORRECTION

PATENT NO. : 9,938,580 B2
APPLICATION NO. : 14/384955
DATED : April 10, 2018
INVENTOR(S) : Benjamin Meder et al.

It is certified that error appears in the above-identified patent and that said Letters Patent is hereby corrected as shown below:

Column 32,
Lines 1-2, In Claim 8 "wherein the therapy monitoring comprises" should read -- where the method comprises --.
Line 3, In Claim 8 "therapy effects or method." should read -- therapy effects or therapy outcome. --.

Signed and Sealed this
Ninth Day of April, 2019

Andrei Iancu
*Director of the United States Patent and Trademark Office*